(12) United States Patent
Johnson

(10) Patent No.: US 7,477,285 B1
(45) Date of Patent: Jan. 13, 2009

(54) NON-INTRUSIVE DATA TRANSMISSION NETWORK FOR USE IN AN ENTERPRISE FACILITY AND METHOD FOR IMPLEMENTING

(75) Inventor: Steven Johnson, Highland Village, TX (US)

(73) Assignee: Careview Communication, Inc., Plano, TX (US)

( * ) Notice: Subject to any disclaimer, the term of this patent is extended or adjusted under 35 U.S.C. 154(b) by 502 days.

(21) Appl. No.: 10/735,307

(22) Filed: Dec. 12, 2003

(51) Int. Cl.
*H04N 7/18* (2006.01)
*H04N 9/47* (2006.01)
*H04N 5/228* (2006.01)
*H04N 7/173* (2006.01)

(52) U.S. Cl. .............. 348/143; 348/155; 348/222.1; 725/108; 725/133

(58) Field of Classification Search .......... 348/155; 725/108, 111, 133
See application file for complete search history.

(56) References Cited

U.S. PATENT DOCUMENTS

| | | | |
|---|---|---|---|
| 4,608,559 | A | 8/1986 | Friedman et al. |
| RE32,327 | E | 1/1987 | Biba et al. |
| 4,885,795 | A | 12/1989 | Bunting et al. |
| 5,343,240 | A | 8/1994 | Yu |
| 5,574,964 | A | 11/1996 | Hamlin |
| 5,798,798 | A | 8/1998 | Rector et al. |
| 5,995,146 | A | 11/1999 | Rasmussen |

(Continued)

FOREIGN PATENT DOCUMENTS

WO PCT/US/99/21900 9/1999

(Continued)

*Primary Examiner*—David L Ometz
*Assistant Examiner*—Wanda M Negron
(74) *Attorney, Agent, or Firm*—Rudolph J. Buchel, Jr.

(57) ABSTRACT

The present invention is directed to a non-intrusive data transmission network for use in a healthcare facility and method for implementing such network. Each individual patient's room is equipped with a set-top control device, a separate camera, microphone, control module camera control device. The SCD allows for a non-intrusive installation within a minimum amount of time. By utilizing the existing cable television infrastructure, the device creates a high-speed data network throughout the facility. The interface between the SCD and the CCD is accomplished through a standard interface for universally connecting auxiliary devices, such as USB, for enabling expandable, hot-pluggable Plug and Play serial device interfaces. These ports allow external devices such as the camera, microphone, infrared keyboard and privacy control unit to communicate with the SCD. Additional USB ports on the SCD allow for other devices to be connected to the network at a future time. Such devices include those for instrument monitoring, doctor information access or pharmaceutical prescription ordering. Visual information such as e-mail, web browsing, video and audio communications via web camera applications from family members, friends or other parties may be viewed by the patient from the in-room TV set by way of the internal RF modulator (and connecting to the Internet via the patient Internet server). The SCD switches from the standard cable TV channels to the SCD by way of an internal switch controlled by the patient from an infrared control. This control also enables or disables the camera to allow for privacy at times when such privacy is required from external Internet access. The system is configurable to offer this privacy to be layered from specific Internet or external users to the nurses, doctors or security department as the hospital desires.

50 Claims, 9 Drawing Sheets

U.S. PATENT DOCUMENTS

| | | |
|---|---|---|
| 6,195,797 B1 | 2/2001 | Williams, Jr. |
| 6,259,443 B1 | 7/2001 | Williams, Jr. |
| 6,311,268 B1 | 10/2001 | Chu |
| 6,317,885 B1 | 11/2001 | Fries |
| 6,323,897 B1 * | 11/2001 | Kogane et al. .............. 348/159 |
| 6,456,320 B2 * | 9/2002 | Kuwano et al. ............. 348/143 |
| 6,457,057 B1 | 9/2002 | Kageyu et al. |
| 6,529,233 B1 | 3/2003 | Allen |
| 6,757,909 B1 * | 6/2004 | Maruo et al. ................ 725/111 |
| 6,803,945 B1 * | 10/2004 | Needham ................ 348/207.1 |
| 2002/0019984 A1 | 2/2002 | Rakib |
| 2002/0044059 A1 | 4/2002 | Reeder et al. |
| 2002/0069417 A1 | 6/2002 | Kliger et al. |
| 2002/0104098 A1 * | 8/2002 | Zustak et al. ............... 725/131 |
| 2002/0147982 A1 * | 10/2002 | Naidoo et al. ............... 725/105 |
| 2002/0163577 A1 * | 11/2002 | Myers ........................ 348/152 |
| 2003/0025599 A1 * | 2/2003 | Monroe ...................... 340/531 |
| 2004/0075738 A1 * | 4/2004 | Burke et al. ................ 348/143 |
| 2004/0105006 A1 * | 6/2004 | Lazo et al. .................. 348/169 |

FOREIGN PATENT DOCUMENTS

| | | |
|---|---|---|
| WO | PCT/US/02/03805 | 2/2002 |

* cited by examiner

NON-INTRUSIVE DATA TRANSMISSION NETWORK

SYSTEM ADMIN
(CATV HEADEND)

NON-INTRUSIVE DATA TRANSMISSION NETWORK FOR USE IN AN ENTERPRISE FACILITY AND METHOD FOR IMPLEMENTING

BACKGROUND OF THE INVENTION

1. Field of the Invention

The present invention relates to a non-intrusive data transmission network for use in an enterprise facility. More particularly, the present invention relates to a system and method for implementing data transmission capabilities over a cable distribution system.

2. Description of Related Art

Data transmission networks are extremely well known and used throughout the prior art. Network characteristics which differentiate one network from another include: topology or the geometric arrangement of connection devices to the transmission medium; the data transmission technology used for data transfer (transmission protocols are the specification standards for sending types of data); and the substance used for the propagation of signals, i.e., the transmission media. The most common topology or general configurations of networks include the bus, star, and Token Ring topologies. Information networks can also be characterized in terms of spatial distance as local area networks (LAN), metropolitan area networks (MAN), and wide area networks (WAN). For simplicity, the discussion herein will categorize exemplary networks by the substance used for the propagation of signals, i.e., the transmission medium, because, as a practical matter, the threshold inquiry for an enterprise network frequently centers around the transmission media. Such medium substances include copper, e.g., twisted-wire pair, coaxial cable and power, fiber-optic cable, air, dielectric-slab waveguide, and even water. For the purposes herein, only copper, fiber-optic cable and air transmission mediums need be discussed.

Very often the type of transmission medium selected for the network determines the data transmission protocol employed thereon. For example, a local area networks (LAN) is a succession of points, nodes or access port interconnected by a communication line comprised of a specific transmission medium. Most LANs support the bi-directional (two-way) transmission of various data types, e.g., data, still and motion images and voice (sound). A PC LAN that makes use of a twisted pair transmission medium such as CAT 3, CAT 4, CAT 5, CAT 5E or CAT 6 is typically limited to one of the following transmission protocol: Asynchronous Transfer Mode (ATM), the IBM Token-Ring specification (IEEE 802.5), Ethernet standards (IEEE 802.3) including 10Base-T (also called Twisted Pair Ethernet), 100Base-T (or Fast Ethernet), and 1000Base-T (Gigabit Ethernet). The competing standard for Apple Macintosh networks is typically the AppleTalk network system (Apple Macintosh and AppleTalk are trademarked by and available from Apple Computer Inc., Cupertino, Calif.). The network types, transmission medium types and transmission protocols discussed herein are merely exemplary and not intended as an exhaustive list of all possible types. Moreover, those ordinarily skilled artisans in the relevant art will recognize that other exemplary types are presently known or will become known in the future. These examples types are proffered only for clarity and not intended to limit the scope of the present invention.

Similarly, a LAN which makes use of coaxial cable may utilize one of the above identified transmission protocols. A LAN using AC power lines as its transmission medium may utilize the CEBus transmission standard (Consumer Electronics Bus, which is a trademark of and available from Electronic Industries Association Corporation, Washington D.C.). LANs operating over air transmission mediums employ any of a group of competing protocols under the IEEE 802.11 standard.

Data distribution systems are likewise extremely well known and used throughout the prior art. Data distribution systems differ from data networks in that data distribution systems were initially uni-directional, but recently that distinction is somewhat less accurate because of the trend toward the bi-directional transmission of data. Data distribution systems were initially intended for the uni-directional broadcasting of television and radio media from a common source or, alternatively, transmitting captured surveillance images to a common source. Data distribution systems are also distinguishable from networks in that they are generally configured as star topologies, or bus, but cannot be configured in a true ring topology. Data distribution systems also require transmission media having large bandwidths which typically restrict the transmission medium to coaxial cable and fiber. Exemplary distribution systems includes community antenna television or community access television (CATV), master antenna television (MATV), small master antenna television (SMATV) and closed circuit television (CCTV).

With the exception of CCTV, each of the above identified types of distribution systems are dependent on a broadband transmission medium, while LANs may be successfully operated over a less expensive twisted pair media. As a practical matter, while LAN components were once widely available with BNC connectors (British Nautical Connectors), presently virtually all LAN network components are ported with RJ-45 eight conductor twisted pair connections. CCTV distribution systems, which are largely relegated to surveillance systems, are a mix of coaxial, and 4, 6 and 8 conductor twisted pair media.

Therefore, in the event that an enterprise resolves to wire a transmission network over an existing facility, typically the most expeditious and cost effective means is by routing a twisted pair CAT medium throughout the existing structure. Conversely, if an enterprise decides to install a surveillance network in an existing facility, the most expeditious and cost effective means is by routing a dedicated coaxial cable for the distribution system. This often results in three separate and independent wiring networks, comprised of three different transmission media, each employing a disparate transmission technology over virtually the same area of the facility. Still more paradoxically, each of the networks may be ported in essentially the same location the facility for connecting to a specific device.

When taken separately, the cost of implementing any of these wiring networks in an existing facility must be strictly scrutinized not only due to their inherent cost of ownership, but also due to the expense of lost productivity during installation and the long term expenses associated with maintaining two or three separate networks which, essentially, may overlay one another in the facility.

SUMMARY OF THE INVENTION

The present invention is directed to a non-intrusive data transmission network for use in a healthcare facility and method for implementing such network. Each individual patient's room is equipped with a set-top control device ("SCD"), a separate camera, microphone, and control module, camera control device ("CCD"). The SCD allows for a non-intrusive installation within a minimum amount of time. By utilizing the existing cable television infrastructure, the device creates a high-speed data network throughout the facility.

The interface between the SCD and the CCD is accomplished through a standard interface for universally connecting auxiliary devices, such as a Universal Serial Bus ("USB") for enabling expandable, hot-pluggable Plug and Play serial device interfaces. These ports allow external devices such as the camera, microphone, infrared keyboard, and privacy control unit to communicate with the SCD. Additional USB ports on the SCD allow for other devices to be connected to the network at a future time. Such devices include those for instrument monitoring, doctor information access or pharmaceutical prescription ordering. The SCD also contains the main embedded processor board, optional hard disk drive and data to cable communications modulator (modem). This basic platform thus allows communications to the hospital's internal network, as well as to the Internet via the cable distribution system through the cable headend and system administration interface. Communications back to the individual hospital room can be retrieved or viewed via one of the four USB ports. Visual information such as e-mail, web browsing, video and audio communications via web camera applications from family members, friends or other parties may be viewed by the patient from the in-room TV set by way of the internal RF modulator (and connecting to the Internet via the patient Internet server). The SCD switches from the standard cable TV channels to the SCD by way of an internal switch are controlled by the patient from an infrared control. This control also enables or disables the camera to allow for privacy at times when such privacy is required from external Internet access. The system is configurable to offer this privacy to be layered from specific Internet or external users to the nurses, doctors or security department as the hospital desires.

The infrared control allows the patient to use a keyboard to access their e-mail or browse the Internet, etc. from their bed. Additionally, a port may be dedicated to the interconnectability of other devices for the user to interface with the SCD using RF, such as by using Bluetooth or the IEEE 802 standard.

At the hospital's demarcation point of the cable television plant, a cable data control device is installed, as well as a server that interfaces with the existing hospital's network, or it can operate as a stand-alone device. Internet access can be obtained from various sources; wireless, through the present network, or direct connection to local carriers, as in a T1 Line or broadband cable.

The system contains elements that support the nurses' station, doctor's use, hospital administration, security department or any other hospital department wired for cable. The nurses' station is equipped with a touch screen monitor and controller. This nurses' station ties into either the existing hospital network or directly to the server at the demarcation point or may connect to a combination of hospital coaxial cable and hospital ethernet networks. All the rooms can be monitored at the same time or be individually displayed. All layers and entry to the system are password protected to offer a high level of security from unauthorized users.

The doctor's station contains a layout of each room in the hospital. Upon selection, the live camera footage is displayed to the right.

The system also acts as a security device. Each room is monitored for movement beyond the normal movement of the patient. If the system detects a person in the room from movement outside the patient's area, the SCD records the activity and sends it to the server or holds it resident on the internal hard disk drive. Security video may be stored at the security facility or warehoused at a third-party storage facility via the Internet.

BRIEF DESCRIPTION OF THE DRAWINGS

The novel features believed characteristic of the present invention are set forth in the appended claims. However, the invention itself, as well as a preferred mode of use, further objectives and advantages thereof, will be best understood by reference to the following detailed description of an illustrative embodiment when read in conjunction with the accompanying drawings wherein:

Other features of the present invention will be apparent from the accompanying drawings and from the following detailed description.

DETAILED DESCRIPTION OF THE INVENTION

Figure 1A:
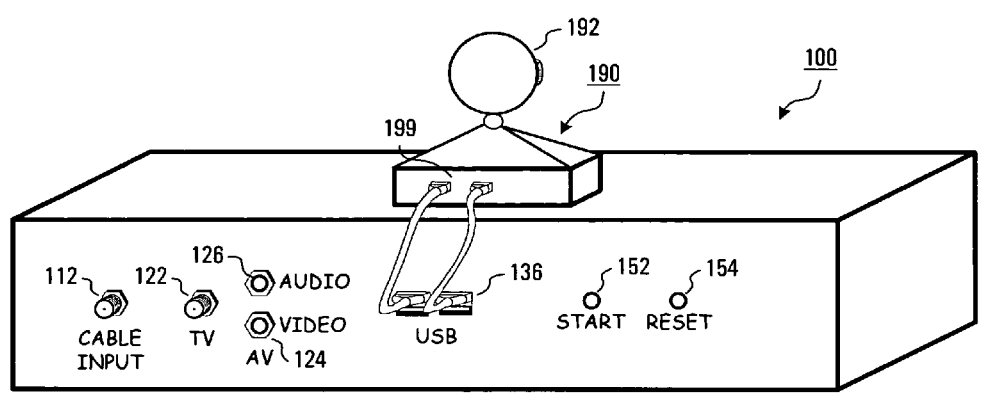
FIG. 1A is a rear oblique view of a set-top control device (SCD) and an auxiliary unit in accordance with an exemplary embodiment of the present invention.
Figure 1B:
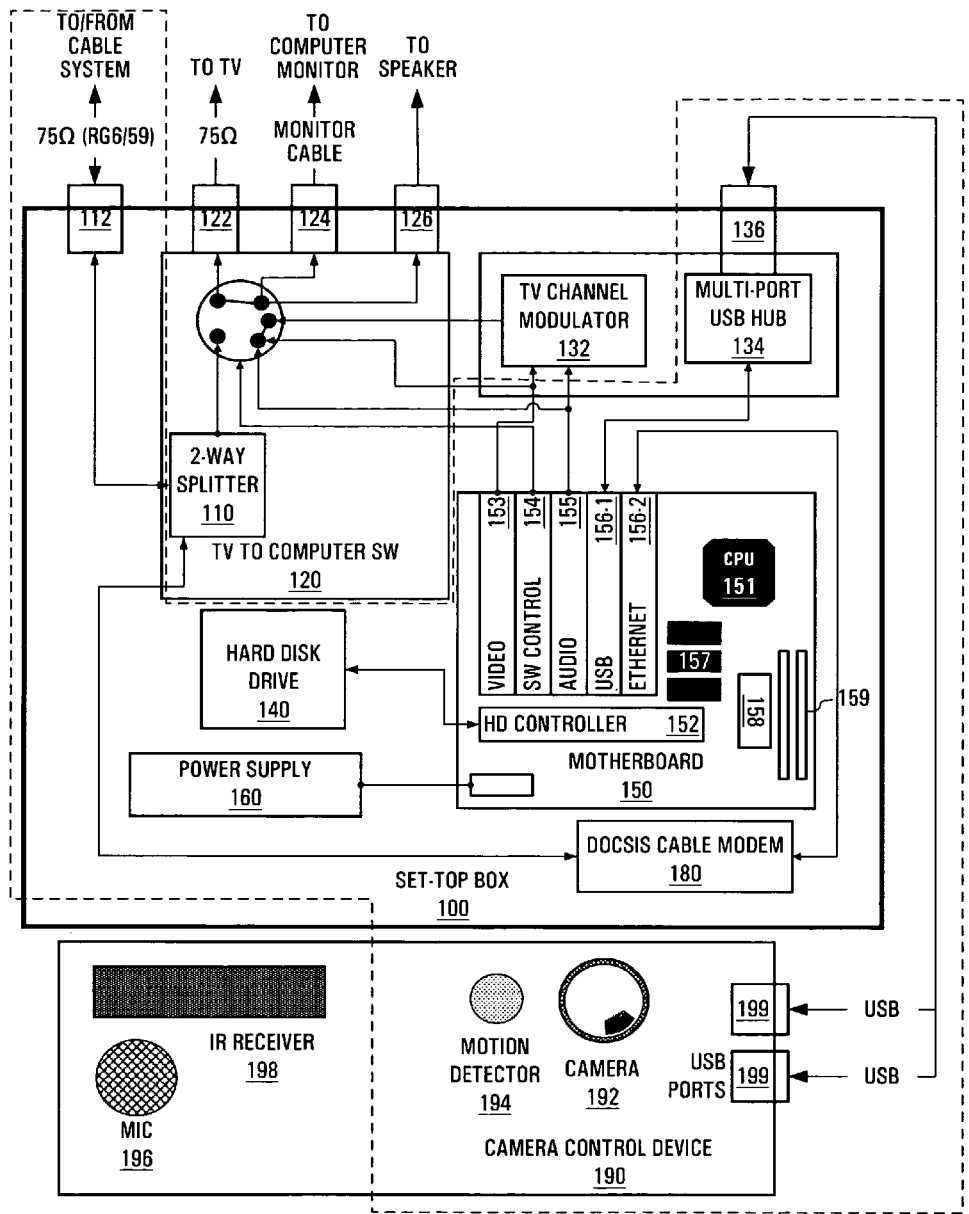
FIG. 1B is a block diagram of the internal components of a SCD connected with a camera control device (CCD) in accordance with an exemplary embodiment of the present invention.

The present invention is directed to a non-intrusive data transmission network which may be deployed over existing coaxial cable within a hospital or similar facility. Each individual room is equipped with a set-top control device ("SCD") and various peripheral devices including, but not limited to, a separate camera, microphone, control module and camera control device ("CCD"). The SCD allows for a non-intrusive installation within a minimum amount of time. By utilizing the existing cable television infrastructure, the device creates a high-speed data network throughout the facility. The SCD, and its peripheral devices, are further described below as depicted in FIGS. 1A and 1B. The exemplary embodiments of the present invention incorporate flexible delivery platforms targeted to offering a solution to the task of getting controlled video back to a central processing point or the Internet. One advantage of the present invention is that it offers healthcare facilities (HCF) a turnkey solution to data monitoring. In bundling the necessary elements needed to accomplish this advantage, the present invention also lends itself to a host of other duties.

FIG. 1A is a rear oblique view of set-top control device 100 (SCD 100) and camera control device 190 (CCD 190), while FIG. 1B is a block diagram of the internal components of SCD 100 connected to CCD 190 in accordance with an exemplary embodiment of the present invention. The interface between CCD 190 and SCD 100 is accomplished by using a Universal Serial Bus through USB ports 199 and 136, respectively. Those of ordinary skill in the relevant art will readily understand that a USB is merely a peripheral bus standard which acts as a plug-and-play interface between a data processing system and various add-on or peripheral devices (such as cameras, microphones, keyboards, telephones, scanners, printers and special purpose devices). The present invention may support either the USB 1.1 or USB 2.0 standard, although USB 2.0 has vastly more bandwidth than the USB 1.1 with transfer rates of 480 Mbits/sec as opposed to 12 Mbits/sec for the USB 1.1 standard. In any case, it is expected that the multi-port USB hub 134 will support both USB 1.1 and the hi-speed USB 2.0 standards which are presently available and the proposed but not fully implemented USB On-The-Go standards (USB portable device standard) for regular and hi-speed data transmissions. Those of ordinary skill in the relevant art will readily appreciate that the depiction of USB is merely exemplary and other peripheral bus standards may be used, for instance the IEEE 1394 standard. With regard to the depicted exemplary embodiment, USB ports 136 and 199 allow camera 192, microphone 196, infrared keyboard (not shown), and privacy control unit (not shown) to communicate with SCD 100. Additional USB ports 136 on SCD 100 allow for other devices to be connected to the network in the future. Exemplary devices include those capable of instrument monitoring, caregiver information access and/or secure pharmaceutical prescription ordering.

SCD 100 also generally comprises main embedded processor board 150 which is coupled to "TV to computer switch" 120, power supply 160, optional hard disk drive 140 and data to cable communications modulator (modem) 180. Modem 180 supports the Data Over Cable Service Interface Specification (DOCSIS) which, as those of ordinary skill in the relevant art will readily understand, is a standard interface for cable modems that manages incoming and outgoing data signals over a cable television distribution systems (or CATV). This basic platform, as will be discussed in greater detail below, allows communications to the healthcare facility's internal network, as well as to the Internet. Processor board 150 is similar in many respects to a generic PC motherboard for a personal computer such as the D865* and D875* class of motherboards (available from Intel Corporation, Santa Clara, Calif.) which support the Pentium 4 (800, 522 and 400 MHz FSBs) and Celeron (400 MHz FSB) CPU processors (both trademarked by and also available from Intel). Those of ordinary skill in the art will readily appreciate that, with respect to a PC, a typical motherboard is the primary printed circuit which contains sockets that accept additional boards. The motherboard contains a variety of similar embedded components, such as those shown on processor board 150. These components include CPU 151, chipset 157, BIOS 158, bus slots (153-156), memory sockets 159 and other embedded controller circuits (depicted in the figure as HD controller 152) for standard peripheral devices such as a keyboard, mouse and printer (not shown), and disk memory devices such as hard disk drive 140. Processor board 150 may also have embedded (built-in) controllers for modem, sound, display and network/bus support, but as illustrated in the exemplary embodiment depicted FIG. 1B, the controllers are embodied on extension cards plugged into AGP, PSA or ISA slots on processor board 150. Typically, a video circuitry 153 is connected to processor board 150 through an AGP slot (when not embedded in the board), while other expansion circuitry is connected through either PSA or ISA bus architectures (e.g., SW controller 154, audio 155, and bus controllers USB 156-1 and Ethernet 156-2).

It is expected that, in most applications, processor board 150 will function similarly to a computer in that at start-up CPU 151 executes software from BIOS 158 that contains all the code required to configure and control the primary devices connected to the motherboard (e.g., the keyboard, screen, drives, serial communications, etc.). BIOS 158 is also used for loading and running software, specifically on an operating system (residing on hard disk drive 140). Other higher level programs and drivers also reside on hard disk drive 140 for operating the attached devices. These include utilities used for running audio, video and SW 120, as well as other devices connected to processor board 150 through USB hub 134 which will be discussed below.

SCD 100 also includes components not found in a conventional computer. These components include two-way splitter 110 coupled to the HCF's cable system (usually consisting of 75 ohm coaxial cable, typically either RG6, RG59 or, occurring more frequently, 500 or 750) through F-type connector 112. Two-way splitter 110 divides the information pathway from connector 112 between SW 120 and DOCSIS modem 180, preferably using coaxial or shielded cables.

Figure 1C:
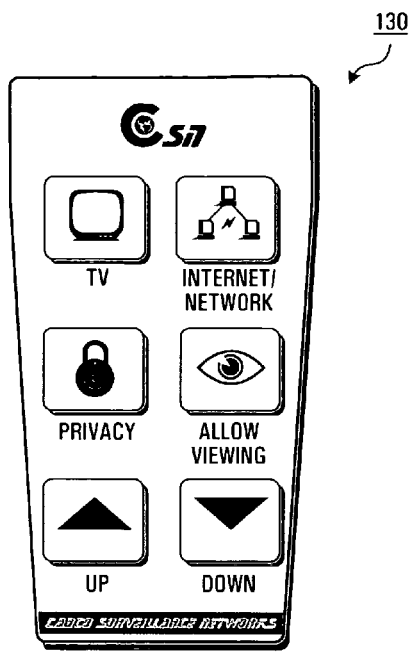
FIG. 1C is an infrared remote control for operating the SCD, television and/or similar devices in accordance with an exemplary embodiment of the present invention.

User control signaling to SCD 100 is accomplished through the use of remote control 130 as shown in FIG. 1C. The TV option allows the patient to access the local television stations and cable distribution systems. The Internet/Network option allows Internet browsing on the Web. The Privacy option blocks anyone from viewing the patient, whether via the Internet or from within the hospital itself. Nurses and doctors that have access rights will be able to override the Privacy button when necessary if the hospital so wishes the privacy feature to function in this manner. Allow viewing enables family and friends who are given the password to open a live videoconference with the patient through the Internet. The Up and Down options are two additional buttons that may be customized to each hospital's preferences and specific needs.

SW 120 is controlled by privacy switch control 153 which translates IR signals from IR receiver 198 into switch positions to SW 120. For example, if the patient desires to watch television, the patient selects the "TV" option on handheld remote control 130 (shown in FIG. 1C) and SW 120 routes RF signals from the HCF's cable system through 2-way splitter 110 to SW 120 and into the patient's television via output connection 122. It is expected that in most applications the HCF's CATV headend will demodulate individual television channels from the cable service provider and re-modulate them onto bandwidths which correspond to those on a conventional television. For example, each television channel should be re-modulated, if necessary, to 6 MHz of bandwidth between 54 and 1002 MHz (see Table I below for typical cable channel assignments used in North America).

TABLE I

Typical North American Television Channels

| Channels | Frequencies |
|---|---|
| 2-6 | 54 MHz-88 MHz |
| 7-13 | 174 MHz-216 MHz |
| 14-22 | 121 MHz-174 MHz |
| 23-36 | 216 MHz-300 MHz |
| 37-62 | 300 MHz-456 |
| 63-112 | 457-751 |
| 113-158 | 752-1002 |

Alternatively, a cable channel tuner may be internally incorporated in SCD 100 (not shown) for selecting television channels on the HCF's cable system without using the television's tuner. This would allow a cable provider more flexibility in making channel assignments. In that case, the raw video and audio signal would be modulated onto a TV channel using modulator 132 or passed directly to a video monitor as raw video through video port 124, and audio through audio port 126.

Conversely, if the patient wishes to access the Internet through the HCF's cable system, the patient would then select the "Internet/Network" option on handheld remote control 130. In that case, SW 120 routes RF signals from TV channel modulator 132 to the patient's television via output connection 122. These RF signals are transformed from raw video and audio signals output from video circuitry and audio circuitry 155, respectively, on motherboard 150. Browser images displayed from video circuitry 154 originate from two primary sources, remotely from the HCF's intranet/Internet and locally from SCD 100 and the devices controlled locally by the SCD 100. Therefore, in addition to providing television channels to the user, the HCF cable system should also support the movement of downstream data from remote data sources to SCD 100 and upstream from SCD 100 to remote data receptors.

Figure 2A:
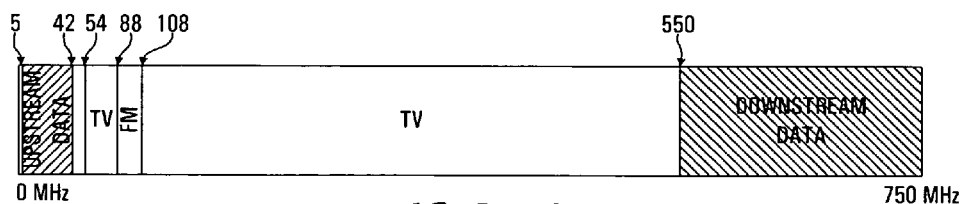
FIGS. 2A and 2B are diagrams illustrating an exemplary spectrum allocation for a cable distribution system.
Figure 2B:
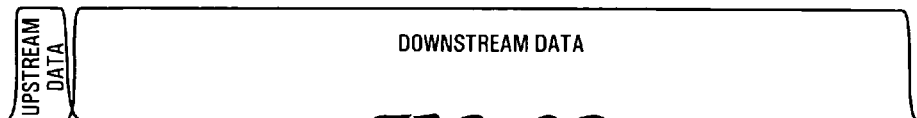

It is anticipated that the present invention will make use of, at least initially, some variant of the DOCSIS standard (data over cable). The following is a general discussion of the functionality of the present invention in a conventional DOCSIS environment; however, those of ordinary skill in the art will understand that the DOCSIS specification may be modified for a particular use environment or an alternative specification for transporting data over selected or custom-developed television cable. The DOCSIS standard recognizes that the upstream data are generally of a different character than that of downstream data; consequently, upstream and downstream data are handled differently. Upstream data from SCD 100 to the cable modem termination system (depicted in FIGS. 3 and 4 as CMTS 310) is in a frequency range of 5-42 MHz (North America) or 5-65 MHz (Europe), while downstream is in a frequency range of 550-750 MHz (North America) (see the spectrum allocation diagrams in FIGS. 2A and 2B). Thus, upstream and downstream data may be simultaneously transmitted and received by modem 180. The upstream data rate for the DOCSIS 1.0 and 1.1 specifications is set by the cable operator and ranges from 320 Kilobits per second (Kb/sec) to 10 Mb/sec (see Table II below). The DOCSIS upstream physical media dependent (PMD) sub-layer uses the frequency division multiple access (FDMA)/time division multiple access (TDMA) burst-access mechanism. Two modulation formats, quadrature phase-shift keying (QPSK) and 16QAM (quadrature-amplitude modulation) with five symbol rates are used which reduces equipment noise in the message at modem 180. The lowest symbol rate supported is 160 KSymbols/sec; the highest symbol rate supported is 2.56 MSymbols/sec under DOCSIS 1.0 and 1.1 (see Table III below).

TABLE II

The DOCSIS Upstream Channel (DOCSIS 1.0 & 1.1)

| Property | Description |
|---|---|
| Modulation | QPSK or 16-QAM |
| Carrier | 5 MHz-42 MHz |
| Bandwidth | Variable, 200 KHz.-3.2 MHz |
| Data Rate | 320 Kbps-10 Mbps |
| FEC | Reed Solomon |
| Encryption | DES |

TABLE III

Upstream Data Rates (DOCSIS 1.0 & 1.1)

| Symbol Rate | Bandwidth Used (KHz) | QPSK Data Rate (Kb/s) | 16-QAM Data Rate (Kb/s) |
|---|---|---|---|
| 160 | 200 | 320 | 640 |
| 320 | 400 | 640 | 1280 |
| 640 | 800 | 1280 | 2560 |
| 1280 | 1600 | 2560 | 5120 |
| 2560 | 3200 | 5120 | 10240 |

Downstream data are sent in fixed size units (204 bytes) so that digital video (MPEG frames) and the data frames can be freely mixed on a single television channel. These units are sent continuously even if there is no data to send so that the system is kept in synchronization. The DOCSIS specification specifies that the images from the Internet are transported via a RF signal as IP packets inserted into MPEG frames (see Table IV below).

TABLE IV

The DOCSIS Downstream Channel

| Property | Description |
|---|---|
| Modulation | 64 and 256 QAM (ITU Annex B with variable interleaving) |
| Carrier | 50 MHz-750 MHz |
| Bandwidth | 6 MHz |
| Data Rate | 27 or 36 Mbps |
| Framing | MPEG-2 |
| FEC | Reed Solomon |
| Encryption | DES |

As can be appreciated from the above discussion, the primary focus of the DOCSIS 1.0 and 1.1 specifications has been that of downstream transmissions (27 or 36 Mb/sec downstream rate in comparison with 320 Kb/sec to 10 Mb/sec upstream data rates). A newer DOCSIS specification supports symbol rates of 5.12 MSymbols/sec using a 128 QAM modulation format which yields 61.44 Mb/sec (see Table V for the upstream data rates supported by the DOCSIS 2.0 specification). This variant of the DOCSIS specification is particularly advantageous for supporting large amounts of the upstream video data incorporating CCD 190 having onboard camera 192 as might be expected in practicing the present invention.

TABLE V

Upstream Data Rates (DOCSIS 2.0)

| Symbol Rate | QPSK (Kb/s) | 8-QAM (Kb/s) | 16-QAM (Kb/s) | 32-QAM (Mb/s) | 64-QAM (Mb/s) | 128-QAM (Mb/s) |
|---|---|---|---|---|---|---|
| 160 | 320 | 480 | 640 | 0.96 | 1.28 | 1.92 |
| 320 | 640 | 960 | 1280 | 1.92 | 2.56 | 3.84 |
| 640 | 1280 | 1920 | 2560 | 3.84 | 5.12 | 7.68 |
| 1280 | 2560 | 3840 | 5120 | 7.68 | 10.24 | 15.36 |
| 2560 | 5120 | 7680 | 10240 | 15.36 | 20.48 | 30.72 |
| 5120 | 10240 | 15360 | 20480 | 30.72 | 10.24 | 61.44 |

FIG. 1B illustrates a typical configuration of the combination SCD 100/CCD 190 as may be implemented in a patient's room. Here, it should be understood that the configuration depicted in FIG. 1B is merely exemplary for the purpose of describing the present invention and alternative configurations are expected. The exemplary CCD 190 generally comprises several input means bundled as a single peripheral input device. These inputs include video (through camera 192), audio (through microphone 196), motion detection (through motion detector 194) and infrared signaling (through an Infrared Data Association (IrDA) compliant IR receiver 198). Additionally, CCD 190 may function as an access point for wireless devices using any of, for example, IEEE 802.11a, IEEE 802.11b, IEEE 802.11g, Wireless Personal Area Network (WPAN), Bluetooth, HOME Radio Frequency (HomeRF) and HIPERLAN, including HiperLAN/2 and HIPERAccess standards, or other alternative wireless USB driven devices can be plugged directly into SCD 100 at USB ports 136. In any case, CCD 190 will receive inputs originating proximate to the patient's room and pass the signals on to SCD 100 over a USB between local USB ports 199 and USB ports 136 on SCD 100. Since CCD 190 is mobile, it may be reoriented for giving camera 192 (and IR receiver 198) direct line-of-sight viewing for various room configurations. While camera 192 is depicted as having a fixed orientation, USB cameras with a remotely USB operable pan and tilt unit, such as the Tracker Cam equipped with a TrackerPod robotic base (trademarked by and available from Eagletron Inc., Toronto, Ontario, Canada) may also be used. USB cameras with user operable zoom lenses are also available.

In operation, CCD 190 receives any of motion, image, audio and IR/RF inputs, which it passes on to SCD 100 for processing and possible transmission onto the intranet of an HCF using its cable system. While each of the logical devices operates independently of one another through the operation of software applications executing from drive 140, inputs received from one device may be used to control other devices. For example, it is expected that, in normal operation mode, camera 192 will be transmitting images onto the HCF's cable system (and possibly intranet) for viewing by authorized personnel, such as nurses and other healthcare professionals. However, a patient may desire some privacy time in which her image is not being transmitted onto the HCF's system. To disable camera 192 from the automated image capture mode, the patient merely selects the "PRIVACY" button on remote control 130 which disables camera 192. As a practical matter, the patient's selection of the PRIVACY button may merely communicate the patient's request for disabling camera 192 to the nurses' station. An attending nurse will then query the patient and disable camera 192 rather than allow the patient to disable the camera directly. As mentioned briefly above, upstream bandwidths are more narrow than downstream bandwidths for the DOCSIS data over cable protocols. Therefore, optimizing the upstream bandwidth is desirable. One method of optimizing the upstream bandwidth is by controlling the transmission of large messages, the largest of which typically consists of streaming image data. The amount of image data transmitted over a network can be reduced by three primary techniques: lowering the image resolution, and hence the packet sizes; lowering the frequency of transmission or frame rate; or by selectively transmitting only higher priority images. For the most part, the former options are not easily managed (i.e., the image resolution (and image quality)) is fixed by the camera, and the maximum transmission frame rate is dictated by CMTS 310 which, by using the DOCSIS protocol, authorizes modem 180 to transmit. However, the latter is achieved by using motion sensor 194 for determining when the image being transmitted should be given priority or elevated to an active state. A software application executing in the background discards most or all of the video data from camera 192 until motion detector 194 is active (i.e., detects motion in the sensing area). In that case, the application then changes the state of image transmission function and sends the video images received from camera 192 over the HCF's intranet. After motion detector 194 returns to its inactivity state (i.e., the activity in the sensing area has abated), the application will continue to send images for a predetermined time period, after which the application will return the image transmission function to a lower state and terminate image transmissions, or transmit them at an extremely low rate (e.g., one frame every five or ten seconds). Alternatively, the transmission states controlled by motion detector 194 will determine the transmission frame rate (fewer frames when motion detector 194 is inactive) or the resolution of the transmitted image (transmitting only a lower quality image when motion detector 194 is inactive) or some combination of any of the techniques discussed above.

Another function of CCD 190 is to receive input data from a variety of wireless devices operating in close proximity to the patient's room. These devices include handheld remote control 130 (shown in FIG. 1C), wireless keyboards, notepad, mice, joysticks, etc., or any type of IR or RF wireless device. Through these devices, a user controls the functionality of the television (on/off, channel selection and volume control, etc.) and myriad computer-executed applications (web browsing, telecommunicating, video meetings via web camera applications with family members, friends or other parties from the in-room TV set, etc.) and even in-room patient services (nurse call button, panic/emergency button, etc.).

Also delineated in FIG. 1B are the components of SCD 100 and CCD 190 necessary for supporting a security control camera (SCC 102). SCC 102 is essentially a stand-alone camera control box which receives its control inputs from the HCF's cable system, and therefore does not utilize all of the user interface peripheral devices used in SCD 100, but may include some or all of them for future applications. Surveillance is also a prime concern in other areas of the hospital, such as the administrative offices, gift shops, cafeteria, parking lots, etc. The primary function of SCC 102 is to acquire surveillance video (and possibly audio) images of a portion of the physical facility and transmit them back to video monitors at a security station in the HCF. With this system implemented, miscellaneous SCC 102 installations, apart from the nurses and doctors, may all be centered at one base station for the Security team to monitor. In accordance with an exemplary embodiment of the present invention, SCD 100 is an outdoor, environmentally controlled camera capable of delivering a multitude of output options to the end user. These output options are: Digital Video, Base band NTSC Video, Agile RF NTSC output from 5 to 42 megahertz, RF Agile Digital Video from 5 to 42 megahertz, DSL telephone or a variety of other RF Wireless technologies. Utilizing one or a combination of any of the above outputs can tailor a system to fit the needs of the end customer or the end customer's infrastructured partner. The system has been designed to co-exist with present CATV plants or telephone companies' infrastructures. In the event that neither the CATV nor the telephone company can be utilized, standard coaxial cable or wireless links can be employed.

SCC 102 may be embodied in a weatherproof, nitrogen-filled camera enclosure (dome) with integrated environmental controls and a digital communications platform. The dome has been designed for use in a variety of applications. As mentioned previously, camera 192 can be utilized inside the dome ranging from fixed or stationery cameras to cameras having pan, tilt and zoom capabilities mounted on a separate base with user-designated orientation capabilities. Camera 192 may also offer digital video outputs and interface with the communications board, which is also housed inside the weather-tight dome. The communications board is a highly robust data radio capable of two-way digital communications via either wireless or coaxial cable. By utilizing the platform, various data cables and bandwidths are selectable to accomplish whatever best fits the applicator's needs. The dome is capable of sending digital video great distances over low cost coaxial cable.

In accordance with other exemplary embodiments of the present invention, SCD 100 and SCC 102 may comprise wireless components as separate Receiver and Transmitter platforms to send and receive data over long distances on several frequency plans (not shown). The system can use any combination of 850-900 MHz-2.4 GHz-2.5 GHz, 5.2 GHz, or 5.8 GHz frequencies to allow communications with the dome (or any other frequency bandwidth available for such types of communications). Presently, the 900 MHz, 2.4 GHz, 5.2 GHz, and 5.8 GHz bands all operate on unlicensed frequencies and are thereby easily deployed, yet do not offer the protection of a licensed frequency band. The 850 MHz and 2.5 GHz bands are both licensed frequencies and must be approved for use by the Federal Communications Commission (FCC). All of the frequency bands allow two-way operations. Various bands are selected determined by distances or interference parameters.

The site security personnel may use one or more SCD 100 for accessing the HCF's cable system to view the surveillance video images, but as will be discussed below, it is expected that the surveillance images will be routed to a computer monitor in the security station over the HCF's Ethernet-based local area network (LAN). As depicted in FIG. 1B, SCC 102 may include only a single camera; however, with the inherent flexibility in the USB 1.1. and USB 2.0 standards, multiple cameras may be serially connected for obtaining multiple perspective views (a single USB port can be used to connect up to 127 separate peripheral devices). However, it should be remembered that the actual number of camera devices connected to SCC 102 is limited by the transmission speed of the bus; the data transmission rate for USB 1.1 is 12 Mb/sec and 480 Mb/sec for USB 2.0, and by the configuration of CMTS 310 (recall that CMTS 310 authorizes the cable modems to transmit which may create still another bottleneck). SCC 102 can be connected to the HCF's cable system at any cable port and begin receiving control signals and immediately transmitting surveillance video. Camera 192 is optionally equipped with remotely adjustable zoom lens for altering the focal length and optically enlarging distance objects. In conjunction with a zoom lens, SCC 102 optionally includes remotely operable USB pan, tilt and rotate unit which enable security personnel to focus the attention of camera 192 on a specific target (not shown in FIG. 1B).

Most healthcare facility administrators have long ago recognized the benefits to their patients of providing cable television and therefore wired the patient rooms with coaxial cable. Typically, each room is also fitted with a twisted pair telephone line (Category 1) which is capable of voice transmission, but not reliable data transmission. Most rooms also have the rudimentary wiring necessary for supporting panic and nurse call buttons and privacy indication lights. This wiring is typically not shielded, nor is it of the quality necessary to support the lessor category 2 (CAT 2) data transmission rates (4 Mb/sec), usually understood as the minimum necessary for data transmission. Thus, in all but comprehensive critical care and post-op rooms, most HCF patient rooms must be retrofitted with Category 5/6 cabling before accessing the HCF's Ethernet-based LAN directly from the room is possible.

Figure 3:
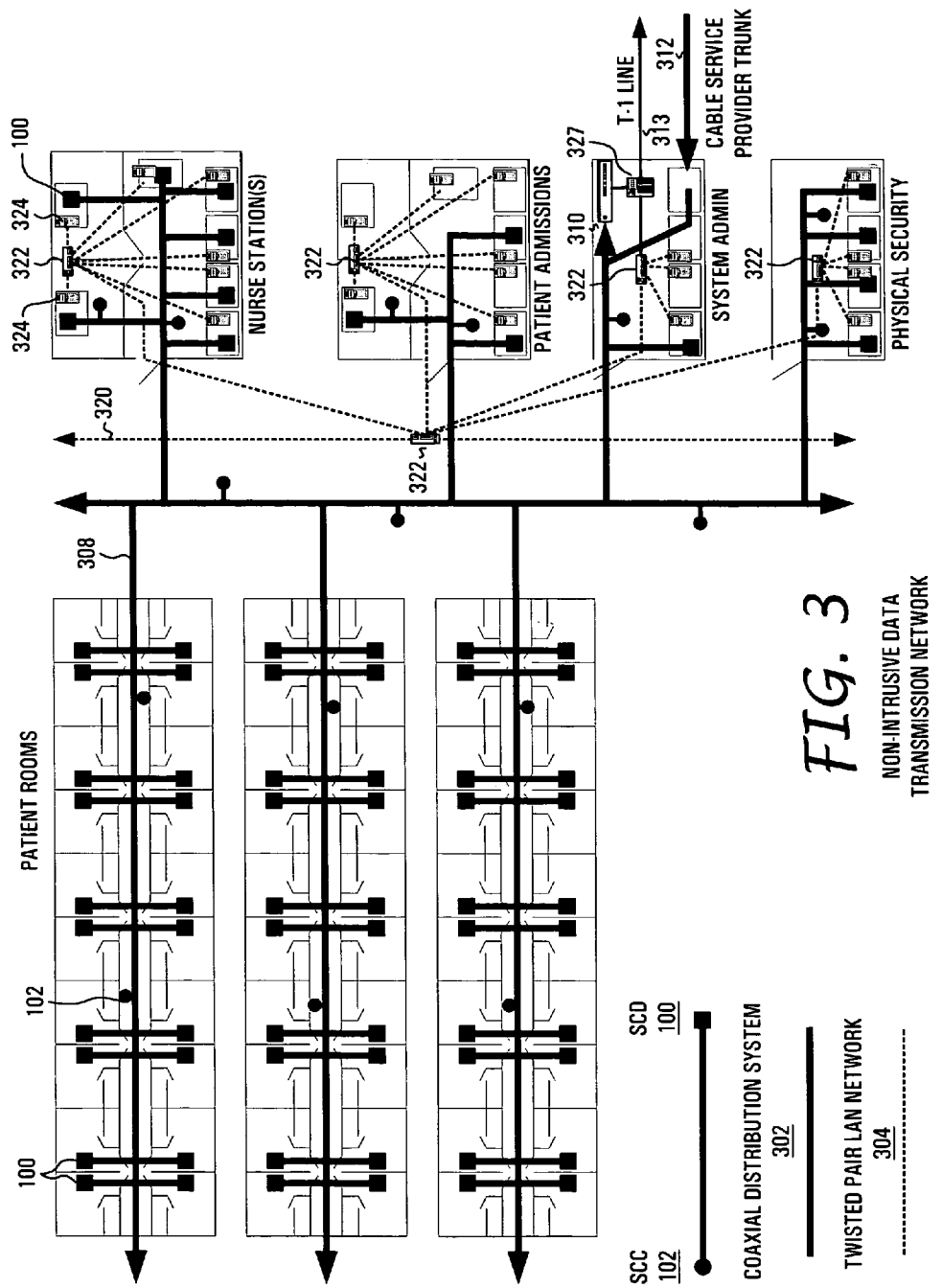
FIG. 3 is a diagram of a partial HCF layout depicting both the existing coaxial cable distribution system topology and the Ethernet network topology in accordance with an exemplary embodiment of the present invention.

FIG. 3 is a diagram of a partial HCF layout depicting both the existing coaxial cable distribution system topology and the Ethernet network topology in accordance with an exemplary embodiment of the present invention. Notice from the figure that the HCF's existing cable distribution system 302 extends to virtually all portions of the HCF, while the twisted pair wired LAN network 304 extends to only certain portions of the HCF. As discussed previously, cable distribution system 302 may comprise any type of coaxial cabling used for cable (CATV) networks, typically a 75Ω internal impedance-shielded or double-shielded, foam core coaxial cable (e.g., RG-6, RG-59 or even RG-11). Connections on coaxial cable 308 are conventionally made through F-type connectors, but also used, though less frequently, are BNC connectors (British Nautical Connectors). Extended run lengths are possible by using low loss RG-6 or RG-11; however, broadband amplifiers (0-1000 MHz range) may be strategically placed throughout cable distribution system 302 to boost signal strengths. Twisted pair LAN 304, on the other hand, typically comprises one of Category 3, 5, 5e, and 6 (CAT 3, CAT 5, CAT 5e or CAT 6) types of unshielded (UTP), overall shielded with shielded individual pairs (STP), or overall shielded (ScTP) stranded and solid copper wire quad-pairs (eight individual conductor wires). Connections on twisted wire 320 are almost universally made through RJ-45 type of connectors/sockets, but Type 1 IBM connectors continue to serve some networks due to their unisex design which enable the same connector to be used for both male and female cable ends. Alternatively, LAN network 304 may comprise a fiber optic network in which messages are modulated onto light waves over glass strands of fiber optic cables rather than as electrical signals over a conductive medium.

LAN 304 generally comprises the equipment necessary for distributing data to each node of network 304 as necessary. For example, the end user typically accesses the network 304 via computer 324 which may be a personal computer, laptop, net computer, or other net appliance capable of processing the information stream. Connections between network branches are accomplished through switches 322. Typically, LAN 304 is a 100BaseT or "Fast Ethernet," 100 Mb/sec version of Ethernet (IEEE 802.3u standard) but may be operate at higher or lower transfer rates using a different transmission standard. Subnets may be implemented within network 302 through the use of one or more routers connected at the network boundaries (not shown). Topologically, each network branch is similar to the other network branches (i.e., the topology of the nurses' station branch is similar to the topology of the patient admission branch is similar to the facility security branch).

The exception is the system administration branch which interfaces with both cable distribution system 302 and external wide area network (WAN) service providers. These generally include a cable television service provider over cable service trunk 312 and an Internet service provider (ISP) over T-1 line 313. In practice, the full twenty-four channels of T-1 access may not be needed, thereby allowing the HCF system administrators to lease some fractional portion of the twenty-four channels (i.e., fractional T-1 access).

Turning now to cable distribution system 302, notice from FIG. 3 that each of the patient rooms are cabled with coaxial cable 308 as part of cable distribution system 302, and further that each room includes at least one SCD 100. Cable distribution system 302 generally comprises the equipment necessary for distributing television channels throughout network 302, including signal splitters, signal amplifiers and connections (not specifically illustrated in the figure). Cable distribution system 302 provides a communications medium to the individual patient rooms, which heretofore has not been exploited to its fullest extent. Implementation of the present invention does not require the use of any special purpose equipment in network 302 between the cable headend and the output nodes. By use of the present invention, prior art cable distribution system 302 becomes a broadband medium for transmissions from a variety of sources, thereby providing visual information such as e-mail, web browsing, video and audio, using SCDs 100, as well as the standard cable TV channels that are typically available over such a network. Moreover, the inclusion of SCDs 100 and SCCs 102 provide system administrators an opportunity to capture and distribute surveillance video (obtained from all or some of the set-top control boxes and security control cameras). Since SCD 100 and/or SCC 102 can be coupled to cable distribution system 302 at virtually any port, the position of surveillance cameras can be positioned and then repositioned anywhere proximate to network 302. Furthermore, surveillance cameras can be positioned up to 98.4 ft. (30 m) away from either SCD 100 or SCC 102 using five cascading USB hubs with 16.4 ft. (5.0 m) buses, or even greater distances using IEEE 804.11 wireless camera peripherals.

It should be understood that the underlying mechanism for supporting the video surveillance system is the use of the TCP/IP protocol suite for establishing and accessing video data generated at a specific nodal location on the network. Each device node on either existing cable distribution system 302 (DOCSIS supported node) or LAN 304 has a MAC address. These addresses are referenced to the physical location of the connection port in the HCF in which the device is coupled. Establishing a TCP/IP session with specific MAC address node is analogous to being connected to the corresponding physical site in the network and bringing up the real-time data being generated by a camera, microphones, etc. at that site. Network nodal sites or establishing a TCP/IP session with a MAC address at the node are password protected. With respect to patients' in the HCF, at check-in they will receive a URL (Uniform Resource Locator) address, room number, and a password for access data to be transmitted by the SCD in that room. Anyone knowing the URL address and password will be able to navigate to the web page, and then log into the surveillance video data stream coming from that patient's room.

Figure 4:
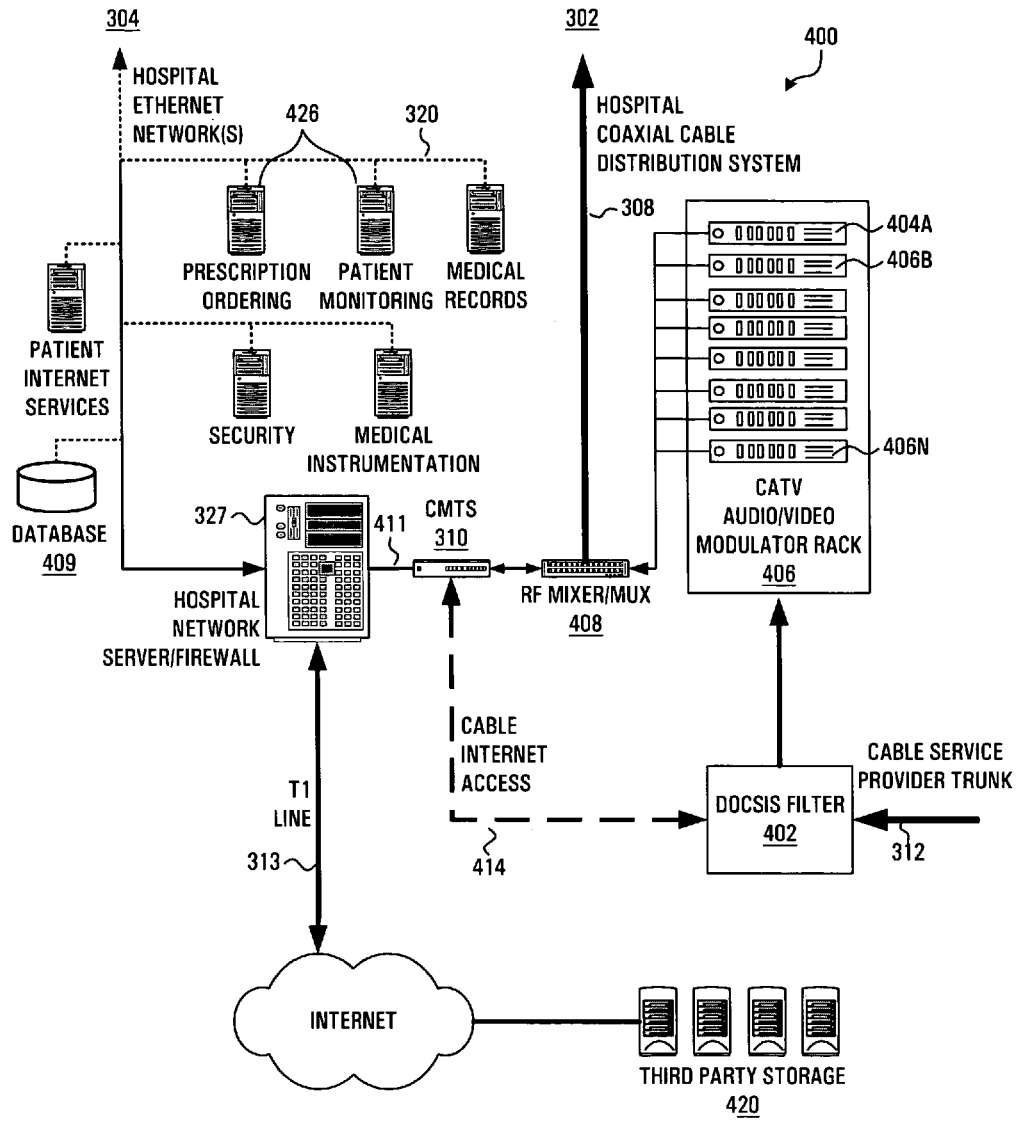
FIG. 4 is a diagram of the headend of a CATV network (cable television plant) which includes network server support in accordance with an exemplary embodiment of the present invention.

With regard to the system administration branch portion of networks 302 and 304, FIG. 4 is a diagram of the headend of a CATV network (cable television plant) which includes network server support in accordance with an exemplary embodiment of the present invention. Headend 400 might be described as the interface between two local networks and two or more wide-area networks (WANs). The two local networks are cable distribution system 302 and LAN 304 discussed above. The two WANs are the cable service provider network, via trunk 312, and the Internet using T1 line 313 leased from an ISP.

Key to managing the interface and corresponding data flow between cable distribution system 302 and the HCF's existing data network, LAN 304, is CMTS 310 (cable-modem termination system). CMTS equipment is physically located at headend 400 and provides the functionality necessary for allowing data to traverse the disparate networks and provides access to the Internet and other data communications to users connected to cable distribution system 302. CMTS 310 includes both a downstream transmitter for generating the modulated RF signals for modem 180, as discussed above with respect to SCD 100, and an upstream receiver for receiving the signals generated by any of the SCDs 100 and CCDs 102. The downstream and upstream signals are combined by a diplexer and routed into the HCF cable distribution system 302 via MUX 408. CMTS 310 is further coupled to firewall/server 327 of Ethernet network 304 through the network-side interface (NSI), a 100Base-T connection, via line 411. Server 327 provides internal firewall protection for implementing security policies designed to secure both networks 302 and 304 from intrusions originating on T1 line 313 and the Internet. Server 327 may also be configured to provide internal firewall protection between individual servers 426 which support HCF enterprise functions such as medical records, patient monitoring, prescription ordering services, facility security and medical instrumentation, for example, and from other users on cable distribution system 302. It is expected that the ISP will provide service on T1 line 313, but alternatively, the ISP may provide Internet access via wireless feed through the present network or through cable trunk 312. In that case, DOCSIS filter 402 will filter data from cable trunk 312 and pass it on to CMTS 310. Firewall protection should be integrated at line 414 prior to entering CMTS 310. Depending on downstream channel(s) selected for network 304, external upconverters may be necessary to remodulate the channel between the downstream transmitter in CMTS 310 and network 302 and/or DOCSIS filter 402. It should be noted that a cable service ISP provider will rarely achieve QoS of a standard T1 or fractional T1 connection due to the need for consolidated firewall protection. Another alternative is to use a wireless connection to the ISP. In that case, a wireless receiver/transmitter is connected to server 327 through the firewall.

Headend 400 also includes the audio/video equipment necessary for selecting television channels from the cable service provider and re-modulating the selected channels onto different channel assignments on network 302. This includes one re-broadcast CATV demodulator 404 for each of the N selected channels on network 302. demodulator 404A-N are typically mounted in rack 406, the outputs of which are connected to RF mixer/MUX 408 for mixing the separate channels, including upstream and downstream data channels.

Finally, in accordance with another exemplary embodiment of the present invention, server 327 may access third-party storage 420 for warehousing surveillance video data. It is expected that the amount of surveillance video data generated by the numerous SCDs 100 and SCCs 102 will be enormous and the relevance of the real-time video data may not be immediately apparent, or relevant video images may be missed or overlooked by HCF staffers monitoring the video. Therefore, the captured video data is temporarily stored on network database 409 contemporaneously with viewing the data and remains on database 409 until off-peak hours. Server 327 then transfers the video data to third-party storage 420 without disrupting normal data traffic.

Essentially, the central platform allows for multiple operations to co-exist on cable distribution system 302, and also on LAN 304. Internet based server 327 continually takes snapshots at each camera (location) and simultaneously stores them on hard disk drive 409. The captured real-time video is accessible by anyone with the inherent rights and connection to network 302, LAN 304 or an Internet connection. An exemplary authorization hierarchy proceeds as follows: public; patient; HCF staff level 3; HCF staff level 2; system administrator; site security; and HCF staff level 1, from least to most access authority. For example, certain real-time video views may be accessible to anyone from the HCF's home page, such as the front façade of the HCF building, a panoramic view of the HCF campus and/or scenic vistas taken from the HCF campus. These images are typically captured by one of the SCCs used by the HCF site security. At the next level, patients and visitors in public areas may be given access to images from certain cameras, such as commons, entrances, cafeterias and the like. Typically, these images are limited to the CSD in the patient's room, the nurses' station, SCCs located in common areas and those areas accessible to the public. The surveillance video generated in patient rooms is triple secured. Someone desiring to view video for a SCD in a patient room must know the URL address and room number for the patient's room and the current password before being authorized by server 327 to access the surveillance video stream from that room. The access authorization for the healthcare facility's staff is based on two criteria: their employment position/duties; and the physical location of their current work assignment. For example, level 3 staffers, such as nurses, technicians and specialists, need to be authorized to view images of only those patients under their care while the patients are located in their work assignment areas, such as the patient's room, treatment and rehabilitation areas, and ingress/egress to those areas. Additionally, level 3 staffers have limited authority to view non-real-time image data from temporary storage database 409, but not from third-party storage 420. Level 2 staffers, on the other hand, are higher level employees and privilege holders, such as doctors and medical specialists who give care to specific patients, regardless of the location of the patient's room in the HCF. Level 2 staffers have limited administrative authority to allow their staff members to view the video of their patients and may view real-time as well as non-real-time image data on temporary storage database 409. Additionally, certain level 2 staffers may have authorization codes for certain patient data on third-party storage 420.

It should be understood that privacy guidelines in an HCF are strictly regulated by rules promulgated under, for example, the Health Insurance Portability and Accountability Act (HIPPA). The capture, transmission, storage and access to patient data must comply with these privacy rules and may require that patient video data be encrypted and patients' identities substituted with unique identification codes prior to storage. In any case, certain HCF employees in non-healthcare employment positions may need a relatively high-level authorization in order to perform their duties, but still be denied access to the actual video images in all but the most extraordinary of circumstances. Thus, system administrators may have limited access to all data on network 302 and in temporary storage 409 and third party storage 420, but not their content. One means of ensuring that system administrators do not make unauthorized use of the surveillance system is to use filter masks and registries. For example, any video data accessed by a system administrator may be checked for quality purposes in its raw form. However, a system administrator's view of patient images is strictly limited. These limitations include lowered image quality (i.e. resolution and size (under 72×36 dpi), short display durations (1-3 sec. maximum), read-only, non-archivable video). Each access is logged into a registry with the administrator's ID and other pertinent information. Site security, the next level, is given authorization for viewing image data from any of the SCCs on the campus, as well as all authorization to operate pan, tilt and zoom features. Additionally, site security is given limited authorization to view unaltered images from any SCD in the HCF. Having an unobstructed view from any vantage point in the HCF is crucial for the safety of the occupants. For example, in case a fire alarm is triggered, the site security is given full access to any camera in any location in order to ensure that all occupants are accounted for. Police, fire and homeland security officials may also be given temporary authorization to use emergency keys, which may be either physical keys or logical password keys. The uppermost tier in the authorization hierarchy is reserved for HCF staff level 1 employees. This group of employees generally comprises high-level executives, administrators and overseers whose duties include reviewing and managing the patients as well as the HCF staff and contractors. Level 1 staffers have access to not only unaltered real-time and non-real-time images, but also to the registry logs associated with the identities of employees who have previously viewed the images. HCF staff level 1 employees are the oversight group which, as a whole, is responsible for scrutinizing patient care, as well as monitoring the conduct of other HCF employees.

Users of devices connected to cable distribution system 302 (or LAN 304) of the present invention generally fall into one of three basic categories: patient; healthcare professional; or security. A patient's access to the network is through a SCD 100 in the patient's room. The authorization rights for the patient are associated with the particular device and password. Healthcare professionals may access the system in a variety of ways, but the scope of their authorization is limited to their level and current work assignment. A doctor may access upstream video on network 302 at various locations in the HCF by merely logging into the system. For example, a doctor may log in at her office on a laptop or PC connected to network 304, or at a remote location, such as an off-campus office or other location over the Internet and across server 327. Furthermore, since the doctor's access authority rests with her login ID and password, a doctor might log into the system in a patient's room using SCD 100 at that site. Server 327 will recognize, that although SCD 100 is assigned to a patient room, the login ID and password received from the SCD authorizes the user greater access than does the room-assigned patient ID and password. Alternatively, the doctor may log in at nurses' stations using a PC connected to LAN 304 or a SCD connected to cable distribution system 302. Security personnel are generally constricted to using only PCs located in the HCF's physical security office in all but the most extraordinary of circumstances. Here again, it should be appreciated that certain HCF cameras will be defined as public accessible will not require a login ID or password, regardless of the type of device accessing the network, (e.g., the HCF front façade, landscape, parking areas, scenic views, etc.)

In any event, primary central server 327 has private control over every camera in network 302. Depending on the installed configuration, this can range from many channels of full motion NTSC Video to many channels of digital video, to both. The primary central system is a real-time display and control system. Each camera can be rotated up to 350 degrees with a zoom of any value from 1 to 300 times the actual size. The camera is also capable of quasi night vision operating in extremely low light situations. All of the cameras' functions are controllable via the primary central server. The primary control system can be configured to store anything from full motion video to still photos on its internal hard disk drive arrays. The primary central server is capable of delivering video or digital outputs to run big screen TVs or projection systems.

Figure 5:
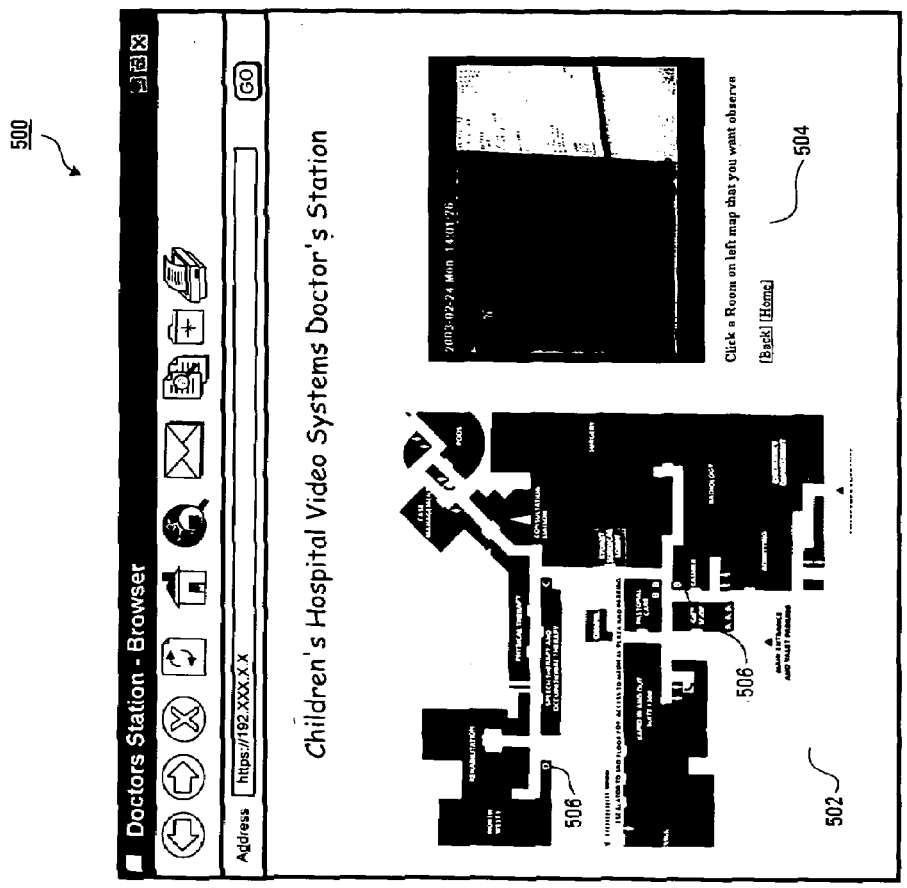
FIG. 5 is an illustration of a screenshot displayed to a healthcare professional in accordance with an exemplary embodiment of the present invention.

A patient's use of SCD 100 has been generally discussed above as having the resources available to the patient over network 302. However, healthcare professionals generally do not access the real-time upstream video on cable distribution system 302, Healthcare professionals generally access this data on devices tied to LAN 304 or directly to server 327 at the demarcation point. The transference of upstream data between cable distribution system 302 and LAN 304 was discussed above with regard to FIGS. 3 and 4. In either case, a healthcare professional-user is presented with a much different interface than a patient. FIG. 5 is an illustration of a screenshot displayed to a healthcare professional in accordance with an exemplary embodiment of the present invention. Here, it should be understood that, while screenshot 500 is described in terms of http-enabled applications (http is a web-based application protocol that runs on top of the TCP/IP suite of protocols), as is the description of the remainder of the present invention, those of ordinary skill in the art will readily appreciate that the video images may be accessed from server 327 using a non-http client application. Authorization to the application's functionality is attained through a browser by entering a URL for the application. The application site is brought up on the browser, the user is queried with "ID" and "PASSWORD" fields. Once logged in, the user will be presented with a screen similar to screenshot 500. Notice that after login the user browser accessed a secure site using Hypertext Transfer Protocol over Secure Socket Layer (https or http over SSL). https encrypts and decrypts are user page requests as well as the pages that are returned by server 327. While it may not be strictly necessary to utilize SSL for devices on LAN 304, https should be used for accessing confidential video images from the Internet.

Screen is subdivided into two distinct frames: navigation frame 502 and image frame 504. Navigation frame 502 is a graphical user interface (GUI) which depicts a graphic image of the physical layout of the HSF campus or a portion thereof. The user can scale and pan the graphic image and flip to adjacent or layered levels of the graphic using the pointing device. Landmarks are labeled on the graphic images as are "hotspots" with which the user may interact. These hotspots include iconic representations which identify the site locations of cameras in the HCF which the user is authorized to access, such as camera locations 506. The locations of these hotspots on the graphic image change with the user's access authority. The video image depicted in image frame 504 is a real-time image captured from one of camera locations 506 in which the user has authorization to view. The user can click around hotspots on graphic image 502 causing the video images in image frame 504 to change responsively. Additionally, the browser GUI allows the user to navigate to previously accessed camera locations using a "BACK" control on the interface and to a default camera location, predefined as the home camera location, using a "HOME" control adjacent to image frame 504 on the browser. Finally, image frame 504 may be scaled and/or maximized to cover the entire view window of the browser, thereby displacing navigation frame 502. In either case, server 327 will update the picture every so often. The frame rate is dependent on a number of factors including the number of cameras used to connect to cable distribution system 302, how much usage the primary control system needs at the time, and the user's access authority. The refresh frame rate can range from essentially live motion video (30 frames per second) to a new picture every several seconds.

The nurses' system is located at the nurses' station and is used to monitor patients in their rooms. It is equipped with, for example, a touch-screen monitor and controller, or a standard PC with a keyboard and mouse. It ties to either the hospital's existing network 302, LAN 304 or directly to the server at the demarcation point. This allows constant surveillance of the patient and his or her surroundings.

Figure 6:
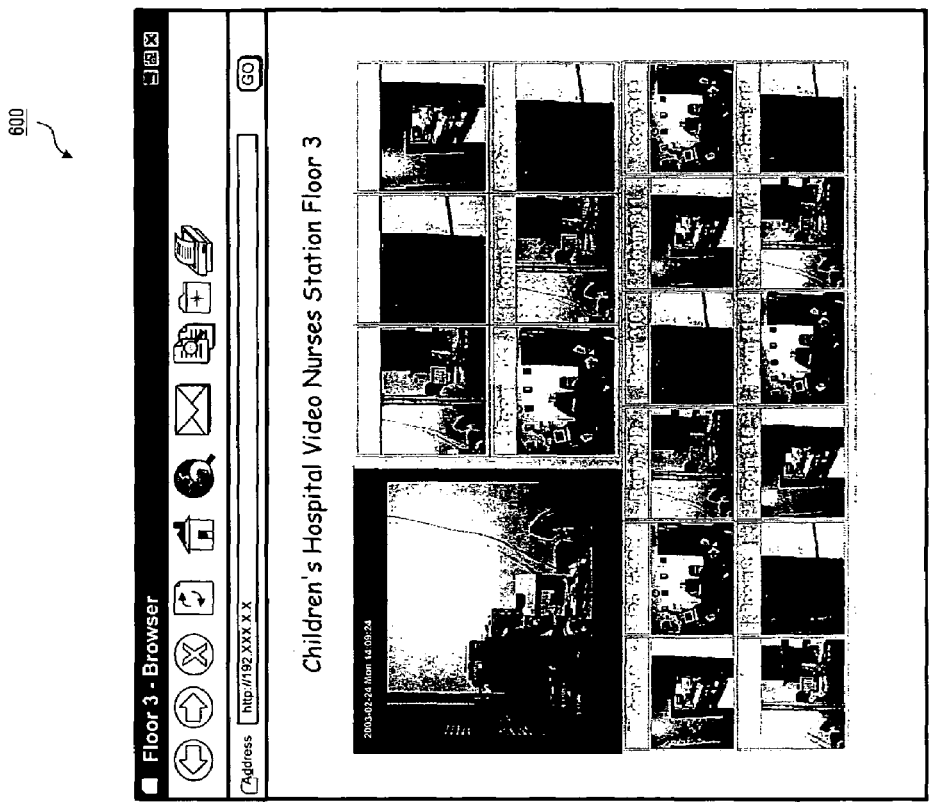
FIG. 6 is an illustration of a screenshot displayed at a nurses' station in accordance with an exemplary embodiment of the present invention.

FIG. 6 is an illustration of a screenshot displayed at a nurses' station in accordance with an exemplary embodiment of the present invention. Screenshot 600 depicts a browser window displaying a plurality of images which were captured at various locations on the third floor of an HCF. Notice that each image frame is identified by the patient room from which it was taken. The frame bar may also include a timestamp to show the precise time the image was taken. This feature may be important in situations where the image frames are prioritized and then transmitted based on motion detection (discussed below). Each frame is scalable and/or may be displayed as a zoom image in a magnification frame. The station allows the medical professionals to view all monitored rooms instantaneously, either at the same time or individually displayed. This creates more attentive care for the patient, as well as better time management for the employees, thus decreasing the amount of time to make rounds.

From this station, the healthcare professional can create a 'hierarchy of rooms' where he/she may arrange the order of care for the patients by placing emphasis on higher need patients. The more attention that is required by a specific patient, the higher they are placed on the screen. Therefore, higher need patients may be monitored more closely than is the standard patient. Nurses, as well as patients, benefit from the system in the nurses' station. This resourceful tool enables more efficient shifts for nurses and a quicker response time to emergencies.

The frame rate onto network 302 may be relatively constant or controlled. In accordance with an exemplary embodiment of the present invention, video image frames are captured regularly and automatically, passed to the network and then used to refresh the images displayed on frame 500. In accordance with an exemplary embodiment of the present invention, the frame rate is not regular and updated video images are controlled at the camera. With regard to this embodiment, CCD 190 (see FIG. 1B) includes motion detector 194. Activating detector 194 signals SCD 100 to transmit the current video image onto cable distribution system 302. In accordance with another exemplary embodiment of the present invention, motion detection is accomplished passively without the use of motion detector 194. By using this technique, a series of image frames are captured by camera 192 and compared to one another. Each frame is compared to the next frame in a sequence of changes which indicate motion in the view area. If a current frame does not differ from the previously saved frame, the current frame is discarded without being saved or transmitted to the network. If a change is detected, then the current frame is not discarded. By identifying only the video images in which some action has been recorded, transmission bandwidth may be conserved over network 302.

With regard to another aspect, image frames which have been identified as showing motion may be saved locally on drive 140 having several benefits. First, if the CMTS has not authorized the SCD to transmit or is temporarily allocating only a meager number upstream spaces, then the motion video data can be transmitted slightly time-delayed. Thus, if the motion captured by the camera is crucial, the data is locally backed up for safety purposes. This feature may also save video image data if the network goes down. Implementation may be performed in several variations. First, a motion detection area on the video frame may be selected. For instance, for addressing security concerns, only the difference outside the patient area might be considered between the two image frames. If differences as detected, that frame is flagged as having a higher priority, time stamped and temporarily saved locally on drive 140. In order to conserve space on the drive, saved video frames will be overwritten, but only after a predetermined time period has elapsed. Prior to that time, the flagged image frames are available to be downloaded or viewed on the television monitor in the patient's room. Alternatively, for addressing patient care concerns, only the differences detected between the two image frames in the patient area might be considered. Movement by healthcare professionals, family members and others who do not cross the path of the patient area will not trigger the image frame to be saved. In either case, the detection of slight motion will generally not cause the video to be saved. However, when the amount of change detected between the current frame and the last saved frames is above a threshold amount, the current frame is saved. These motion detection functions may be incorporated in camera 192, video circuitry 153, or may instead be implemented as a sub-routine of a software application. With this feature in place, it is possible to create a video history of the events occurring within the medical room, which is particularly useful in contrived lawsuits. By viewing the tapes, one can determine all aspects of the situation and in most cases where the true concern lies.

As discussed elsewhere above, infrared sensors, Bluetooth or any other type of wireless USB driven device can be connected directly to SCD 100 using USB port 136 through hub 134, thus giving SCD 100 the ability to communicate with numerous types of IR/RF enabled devices without that device being physically connected to SCD 100 through a USB port.

With HIPAA patient privacy rules in effect, the present invention enables healthcare professionals to comply with the boundaries in place to protect the patient's records. It is now possible to call up and download a patient's chart onto a tablet PC through the HCF's cable distribution system 304. As is well understood, patient information is stored as electronic data at a central database, such as data storage 409. Heretofore, information for a specific patient was typically called up at a docking port located at a nurses' or doctors; station, downloaded onto a laptop, pen device, etc. and then carried into the patient's room for the consultation. Once finished, the healthcare professional exits the patient's room and uploads the update chart information to the system at the same or a different docking port. The present invention allows for this to be truncated while ensuring that the patient's privacy boundary is strictly enforced.

Figure 7:
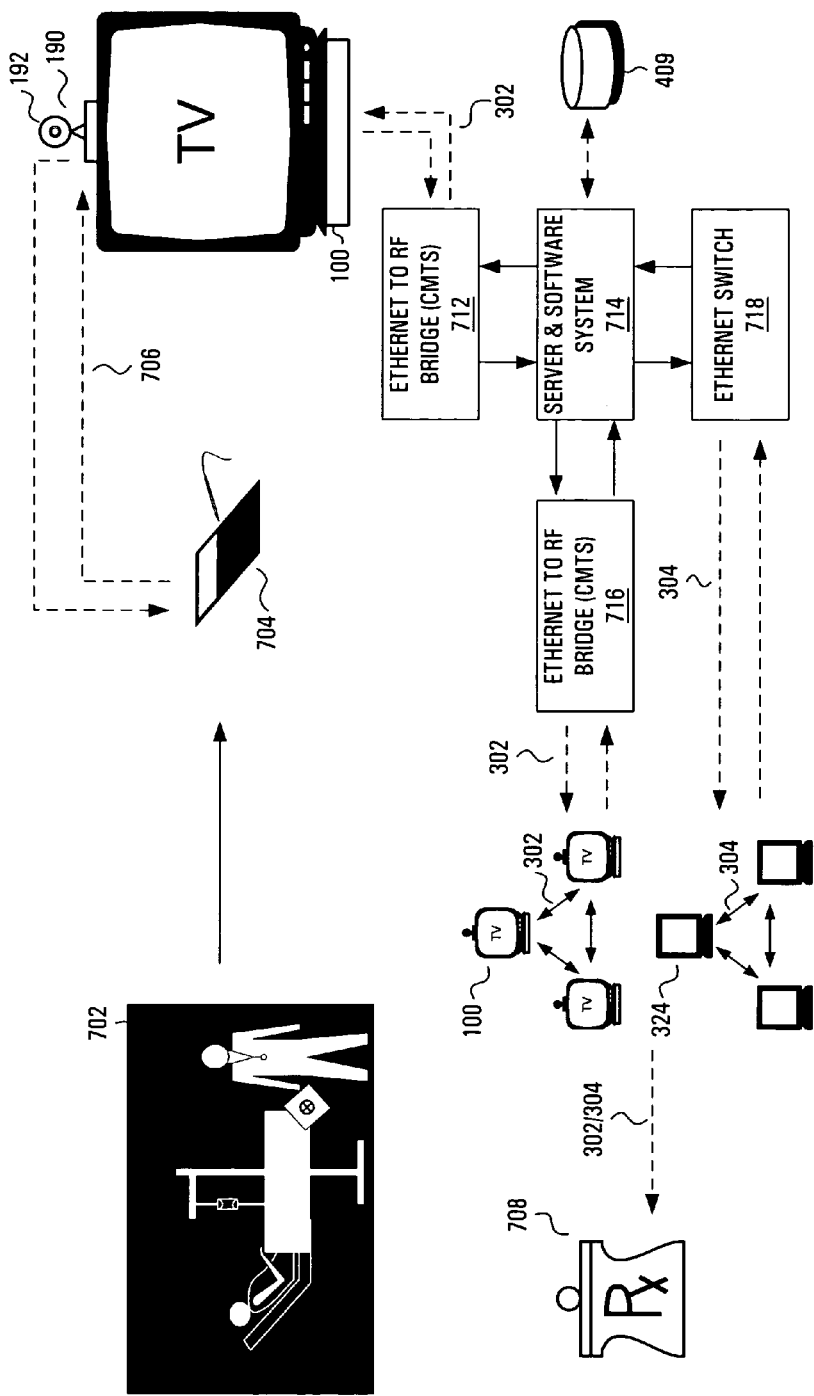
FIG. 7 is a diagram depicting the implementation of wireless devices in accordance with an exemplary embodiment of the present invention.

FIG. 7 is a diagram illustrating a process for implementing a wireless device on an HCF's existing cable distribution system for ensuring a patient's privacy boundary in accordance with an exemplary embodiment of the present invention. In a typical patient room setting 702, as a healthcare professional enters a patient's room, the patient's information is instantly transmitted to IR/RF enabled data processor 704. The process may be completely automated and executed as a background task. In accordance with one exemplary embodiment, as device 704 comes within range of USB driven IR/RF transmitter/receiver 190, device 704 transmits a "ping" over wireless media 706 which is received by SCD 100. Device 704 then handshakes with SCD 100 and a connection request is sent over cable distribution system 302 through Ethernet to RF bridge (step 712) and on to the network server (step 714). The operation of step 712 may be performed by CMTS 310 and the operation of step 714 may be performed by server 327, as discussed with respect to FIGS. 3 and 4 above. Here, it should be understood that the particular SCD in-room 702 is recognized by the network control server as being authorized for access on network 302 through Media Access Control (MAC) address (typically embedded in network card 156-2 (FIG. 1B)). Access to the network is granted or denied based on an access control list (ACL) of MAC address at primary network server 327. If the device's MAC is not listed on the ACL, it must be configured in the ASL, with a password, user ID etc. by someone with system administrator privileges. The MAC address is indexed to patient room 702 and to the name and admission information for the patient occupying patient room 702 in another database. Other devices which attempt to bridge onto network 302 through SCD 100 are also granted or denied access to network 302 based on the ACL of MAC address at a primary network server. These devices are also cross-references to user information and security measures may be implemented to assure the authorized user is operating the device (such as password protection, etc.). Optionally, the user is challenged for a password prior to being granted access to confidential patient information. Thus, at the time wireless data processing device 704 is granted access to the DOCSIS data streams of cable distribution system 302, a direct relationship exists between the healthcare professional in patient room 702 and the patient occupying room 702. The patient's privacy boundary has been preserved and medical records for the patient may be accessed from database 409 and downloaded to wireless data processor 704. Typically, the patient's records are locked at database 409 when an editable copy of the records has been downloaded. This lessens the likelihood that two copies of the same document are edited simultaneously. Once the consultation in-room 702 is complete and the updated patient records in wireless data processor 704 are uploaded back into database 409, the records are unlocked for other users. This feature allows the doctor to attend to patients more quickly, thereby lessening the confusion that may be caused by attending multiple patients.

Notice also that the healthcare professional can communicate directly with any node on HCF's cable distribution system 302 or LAN 304. For instance, should the healthcare professional desire to send a message back to her office computer in the HCF, the message is generated on wireless device 704, passed to CSD 100 over wireless link 706 and onto bridge operation 712 over cable distribution system 302. After the RF DOCSIS-based data is converted to the Ethernet data link protocol format, the message continues to server operations 714 and to Ethernet switch 718 for routing over LAN 304 to the healthcare professional's office computer 324.

Communicating with another SCD from wireless device 704 is also possible from SCD 100, but typically there is no direct communication from SCD 100 to the other SCD (DOCSIS does not support peer-to-peer transactions). The transaction process is essentially identical to that described directly above, except that, rather than the message continuing from server/software operations 714 to LAN 304, the server forwards the message back onto cable distribution system 302 via Ethernet to RF bridge operation 716. The above-described set of operations essentially takes the message from the upstream DOCSIS band on network 304 and feeds it onto the downstream DOCSIS band of the spectrum for delivery to the recipient SCD.

Alternatively, the message recipient may be connected to LAN 304. For instance, should the healthcare professional desire to send a message back to her office computer in the HCF, the generated data on wireless device 704 is passed to CSD 100 over wireless link 706 and onto bridge operation 712 over cable distribution system 302. After the RF DOCSIS-based data is converted to the Ethernet data link protocol, the message continues on to server operations 714 and to Ethernet switch 718 for routing over LAN 304 to the healthcare professional's office computer 324.

In accordance with still another exemplary embodiment, implementation of the present invention on an existing cable distribution system enables a healthcare professional to enter a prescription, lab order or therapy request into the PC tablet and electronically transmit it to the service provider. Using a prescription order as an example, the messaging process flows essentially as described above. The healthcare professional enters a prescription for medication on wireless data processor 704 which sends the data to SCD 100, which places the message in the DOCSIS upstream data flow on network 302. All upstream data is converted to Ethernet data link protocol by Ethernet to RF bridge process 712 and forwarded to server/software processes 714. Here, the message address is checked against network routing tables and forwarded to the network having the pharmacy node address. It is expected that the pharmacy will be connected to LAN 304, as will most other HCF service providers. However, server/software process 714 may route the message to either network (the existing DOCSIS enabled cable distribution system with or the Ethernet LAN) depending on the address. But typically, the message will be forwarded through one or more routers and/or switches 714 prior to reaching the pharmacy node. It is expected that, upon receipt, the pharmacy device 708 will immediately respond to device 704 with a confirmation that the message has been received.

The more popular and utilized wireless technologies are RFID, Bluetooth and barcode scanners. By integrating these technologies with the CSD and the existing hospital cable distribution system with non-intrusively enhanced DOCSIS data transmission capabilities, the applications and resources are thereby expanded through various aspects of daily use. RFID technology can be leveraged at many levels to assist with the flow of business. Parts, item transporters or containers may be identified with RF tags. An RF tag may store information to simply identify its carrier, or it may allow information to be written to it as the carrier flows through a process. RF tags may also transmit on several different frequencies, thereby allowing read and write activity to range from an inch to several thousand feet. These features allow for more extensible use of barcode scanners—via infrared or wire.

Figure 8:
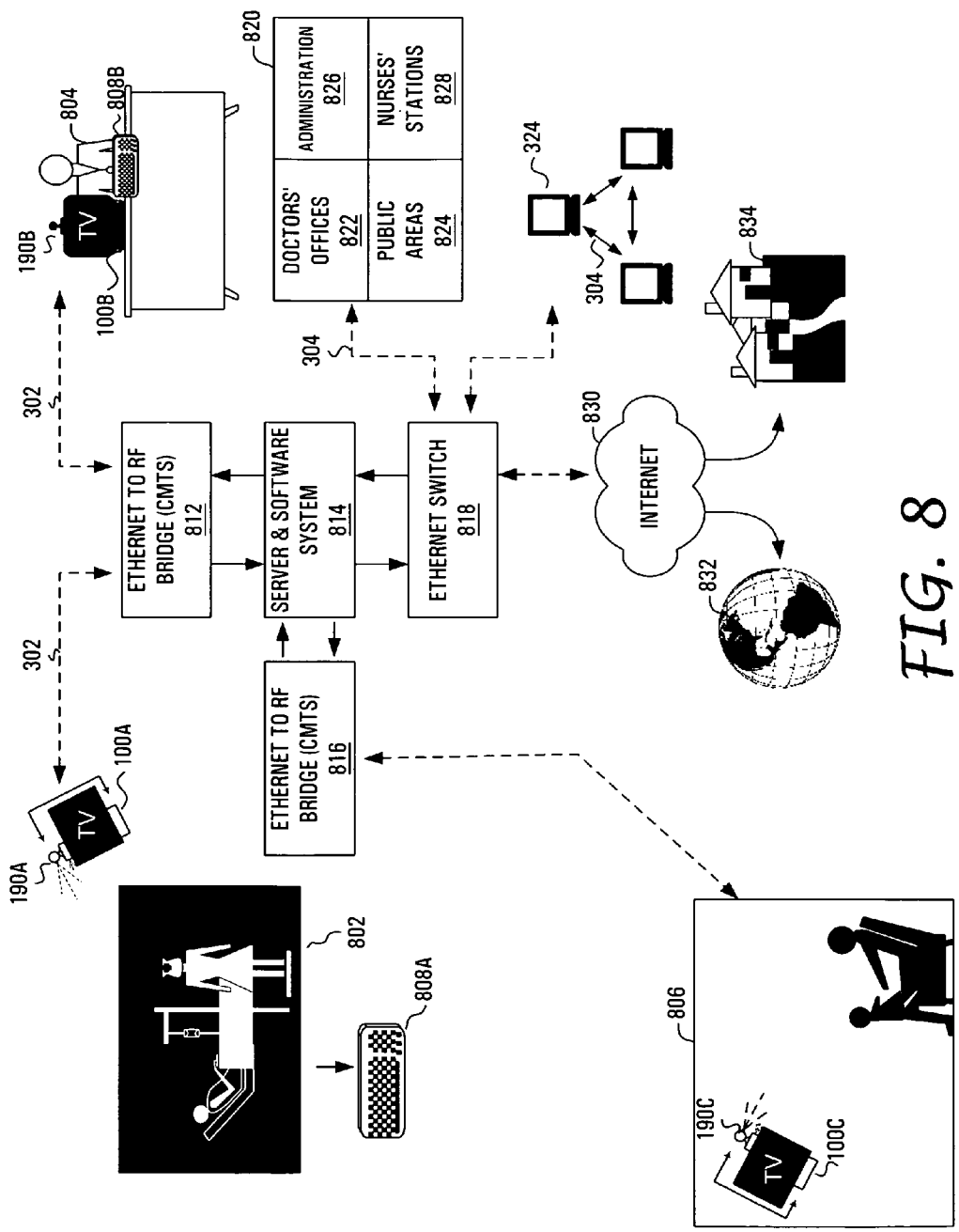
FIG. 8 is a diagram depicting the global application of the present non-intrusive data transmission network invention when implemented over an existing cable distribution system in accordance with an exemplary embodiment of the present invention.

As many medical visits go, the medical professional spends much of their time checking on patients and walking from room to room. However, by enhancing the existing HCF cable system non-intrusively with the presently-described DOCSIS data transmission capabilities, the number of face-to-face patient visits where the professional would physically go into the room could be reduced while the patient could actually receive more personal attention from the professional via the SCD and associated television. FIG. 8 is a diagram depicting the global application of the present invention when implemented in an HCF. In accordance with an exemplary embodiment of the present invention, a system of cameras and microphones are installed across the HCF, even in areas serviced only by the existing cable distribution system 302. These areas may include patient rooms 802, meeting/conference rooms, operating/recovery rooms, waiting rooms 806, doctors' offices 804 and other commons and public areas not typically supported by an Ethernet LAN. By non-intrusively enhancing the existing cable system with DOCSIS data transmission capabilities for supporting data traffic, the HCF essentially increases the coverage of the Ethernet LAN supported applications in the HCF without retrofitting the HCF with twisted wire or fiber cabling. In accordance with one exemplary embodiment of the present invention, infrared control 130 (FIG. 1C) or wireless keyboard 808A allows the patient to access SCD 100A from the comfort of their bed. Wireless keyboard 808A enables patients to check e-mail, surf the Internet and visit with distant family members who have a camera on their own computer.

In accordance with another exemplary embodiment of the present invention, doctors in non-LAN offices, such as office 804, can see and speak with patients or families from anywhere in the hospital, even in other areas not supported by LAN 304. These include patient rooms 802, waiting rooms 806 and other doctors' offices, commons areas, conference rooms without Ethernet LAN connection. The process for creating and managing a video meeting is essentially similar to the process described above for data transmissions. For instance, a healthcare processional in office 804, which does not have an Ethernet connection, desires a conference with a patient's family which is in a waiting room elsewhere in the HCF. Rather than traveling the length of the HCF, on occasion the professional may initiate a videoconference with the occupants of waiting room 806. As discussed above, the professional interfaces with SCD 100B using wireless device, such as keyboard and/or mouse 808B, to initiate the conference request. SCD 100B then sends the request to Ethernet to RF bridge operators 812 over existing cable distribution system 302 in a DOCSIS compliant form. The DOCSIS-based request is received by the Ethernet to RF bridge and forwarded to server/software operators 814 and Ethernet data link protocol message. Server/software operators 814 then locates recipient SCD 100C and attempts to establish a video conference session. The session request is sent to Ethernet to RF bridge operators 816 (which is typically the same CMTS equipment that handled the doctors initiation request) and received by the CSD 100C in waiting room 806. The mechanisms for establishing video conferencing sessions are well known and will not be discussed in detail, but bi-directional data channel paths for video and audio (A/V) data are set up between SCD 100B in office 804 and SCD 100C in waiting room 806 for carrying A/V data in a near real-time manner.

Understanding that the patient-doctor relationship is very important, this feature is not to replace the personal contact, but to complement it. In many circumstances, this feature may be used to announce test or surgical results quicker than before. One such circumstance is immediately after a patient's surgery. After an intense surgical procedure, the family of the patient is often waiting anxiously in waiting room 806, until a doctor or nurse confronts them with the results of the operation. This information is usually given after the doctor finishes, cleans up, and then walks to the waiting room however far away from the operating room that may be. By implementing the present non-intrusive data transmission network for supporting data traffic over the existing cable system, the results may be delivered immediately out of surgery to waiting room 806 from a station that is positioned nearby. The same type of session could be established between patient room 802 and waiting room 806, or with office 804.

In accordance with still another exemplary embodiment of the present invention, real-time audio and video may be communicated to a patient's family members across the world by setting up a bridged communication channel from nodes on the DOCSIS-based existing network 302 and other Ethernet and IP networks. The results of a surgery or procedure may be delivered immediately to family members regardless of geography in the same manner as to those friends and relatives at the HCF. With multiple sessions, family in different countries and family that are in the hospital may see the immediate results of an operation. Moreover, geographically remote friends and family may monitor the patient's progress using the HCF's video surveillance features. As discussed above, during check-in to the HCF, or immediately thereafter, the patient's relatives are given an URL address for the patient's room and a password. That information can then be passed to friends and family with Internet access for access to the surveillance video captured in that patient's room. Typically, the web site will have a room number box, password box, a help button, and an enter button that will direct the family member to the patient.

In accordance with still another exemplary embodiment of the present invention, by implementing the non-intrusive data transmission network for supporting data over the existing cable system as DOCSIS-based traffic, medical monitoring equipment may be uploaded directly to the HCF's network and be available for worldwide distribution. Medical devices such as heart monitors, or any other type of monitoring mechanism, can send data. This data can be used to gather mass amounts of information and then sent to a lab that would in turn study that data. More and more of this equipment is now ported with a USB and therefore may be coupled directly to a USB port on the SCD. Other 100baseT networking which may be bridged to USB and then to the SCD.

The lab could then find patterns in current situations by comparing them to some previous cases. By having all the information in digital form, a computer can search a particular heart rhythm or EEG results and conclude a possible outcome for the patient. The doctor(s) could, for example, find the pulmonary rhythms seen directly before a heart attack in a massive number of cases, and conclude that when the patient to whom they are currently attending is experiencing those same rhythms, they should prepare for a cardiac arrest in a specific amount of time.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A device for implementing video surveillance on an existing coaxial network, wherein the existing coaxial network supports data transmitted over a first carrier signal, a second carrier signal and a plurality of other carrier signals, the device comprising:
    a data port for connecting to the existing coaxial network;
    a modulator for modulating first digital signals onto the first carrier signal, wherein at least some of said first digital signals representing sensory electrical signals, said modulator electrically coupled to the data port;
    a demodulator for demodulating second digital signals off the second carrier signal, said demodulator electrically coupled to the data port;
    a memory for storing sensory electrical signals as data;
    a video sensor for capturing image frames of a surveillance area and for converting said image frames to video sensory electrical signals;
    a motion detector for detecting motion in at least a portion of the surveillance area and issuing a motion indication; and
    a video processor for receiving the video sensory electrical signals representative of the image frames and determining which image frames to save in the memory based on receiving a motion indication.

2. The device recited in claim 1 further comprises:
    an output port for outputting at least said plurality of other carrier signals.

3. The device recited in claim 1, wherein said second carrier signal operates on a carrier frequency between 500 MHz and 1000 MHz.

4. The device recited in claim 1, wherein said second carrier signal is a downstream data over cable service interface specification (DOCSIS) carrier.

5. The device recited in claim 1, wherein at least some of said plurality of other carrier signals operate on carrier frequencies between 50 MHz and 750 MHz.

6. The device recited in claim 1, wherein the video processor is one of a physical component residing in the device, a physical component residing in the video sensor and video processing executable instructions residing in the memory for processing by the logic circuitry.

7. The device recited in claim 1, further comprises:
    an RFID reader for reading RF tags.

8. The device recited in claim 1, further comprises:
    a universal serial bus port.

9. The device recited in claim 1, further comprises:
    an infrared (IR) sensor for receiving infrared signals.

10. The device recited in claim 1, further comprises:
    a medical monitoring device port.

11. The device recited in claim 1, further comprises:
    one of an RF output port, video output port and audio output port.

12. The device recited in claim 1, further comprises:
    a data bus for carrying video information coupled between the video sensor, said data bus being compliant with one of a digital video standard, NTSC video standard, Agile RF NTSC standard, RF Agile digital video standard, DSL telephone standard and USB standard.

13. The device recited in claim 1, wherein the video sensor further comprises:
    a quasi night vision sensor for operating in low light.

14. The device recited in claim 1, wherein said first carrier signal operates on a carrier frequency between 0 MHz and 50 MHz.

15. The device recited in claim 14, wherein said first carrier signal is an upstream data over cable service interface specification (DOCSIS) carrier.

16. The device recited in claim 1, further comprises:
a wireless access point for sending and receiving wireless signals.

17. The device recited in claim 16, wherein the wireless access point is compliant with one of IEEE 802.11, Wireless Personal Area Network (WPAN), Bluetooth, HOME Radio Frequency (HomeRF) and HIPERLAN standards.

18. The device recited in claim 1, further comprises:
a remote user interface for receiving user commands.

19. The device recited in claim 18, wherein the remote user interface further comprises a "PRIVACY" key for disabling the video sensor.

20. The device recited in claim 1, wherein the motion detector is incorporated in the video processor and the video processor compares image frames for changes indicating the presence of motion in the surveillance area between capture of the image frames.

21. The device recited in claim 20, wherein the video processor analyzes a first portion of image frames for changes and disregards a second portion of the image frames.

22. The device recited in claim 20, wherein the video processor selects at least some image frames for discarding based on the comparison of image frames for changes.

23. The device recited in claim 20, wherein the video processor selects at least some image frames for storage in the memory based on an amount of change detected between a current frame and a previous image frame being above a predetermined threshold amount of change.

24. The device recited in claim 1, wherein the memory stores a plurality of executable instructions, the device further comprises:
logic circuitry, said logic circuitry operably coupled to said memory for responding to and processing at least some of said plurality of executable instructions.

25. The device recited in claim 24 further comprises:
an output port for outputting at least said plurality of other carrier signals.

26. The device recited in claim 25 further comprises:
a second modulator;
a switch, said switch electrically coupled between said data port, said output port, and said second modulator.

27. The device recited in claim 26 further comprises:
a tuner for tuning one carrier signal of said plurality of other carrier signals, said tuner coupled to said output port; and
a display for displaying a representation of information on said one carrier signal of the at least said plurality of other carrier signals, said display coupled to said tuner.

28. The device recited in claim 24, wherein said logic circuitry is a central processing unit.

29. The device recited in claim 24 further comprises:
a second sensor for receiving second sensory inputs and for converting said second sensory inputs to second sensory electrical signals, wherein said logic circuitry responds to and processes said second sensory electrical signals for controlling said sensory electrical signals.

30. The device recited in claim 29, wherein the second sensor is the motion detector.

31. The device recited in claim 25 further comprises:
a user interface for converting user interacts to electrical signals, said user interface operably coupled to said logic circuitry.

32. A method for implementing video surveillance on an existing coaxial network having a head-end node and a plurality of distribution nodes, wherein the existing coaxial network supports data transmitted over a first carrier signal, a second carrier signal and a plurality of other carrier signals, the method comprising:
connecting a surveillance device to at least some of the plurality of distribution nodes, said surveillance device comprising:
a data port for connecting to the existing coaxial network;
a first modulator for modulating first digital signals onto the first carrier signal, wherein at least some of said first digital signals representing sensory electrical signals, said modulator electrically coupled to the data port;
a first demodulator for demodulating second digital signals off the second carrier signal, said demodulator electrically coupled to the data port;
a memory for storing sensory electrical signals as data;
a video sensor for capturing image frames of a surveillance area and for converting said image frames to video sensory electrical signals;
a motion detector for detecting motion in at least a portion of the surveillance area and issuing a motion indication; and
a video processor for receiving the video sensory electrical signals representative of the image frames from the video sensor and determining which image frames to save as data in the memory based on the motion indication from the motion detector;
connecting a second demodulator to the head-end node, said second demodulator for demodulating the first digital signals off the first carrier signal;
connecting a second modulator to the head-end node, said second modulator for modulating the second digital signals onto the second carrier signal,
capturing a first image frame from the surveillance area;
converting the first captured image frame to video sensory electrical signals;
modulating the video sensory electrical signals representative of the first captured image frame onto the first carrier signal;
transmitting the video sensory electrical signals onto the existing coaxial network;
capturing a second image frame from the surveillance area;
converting the second captured image frame to video sensory electrical signals;
receiving a motion indication; and
saving the second captured image frame to the memory;
capturing a third image frame from the surveillance area;
converting the third captured image frame to video sensory electrical signals;
receiving a second motion indication; and
saving the third captured image frame to the memory.

33. The method recited in claim 32 further comprises:
connecting a network server to the second modulator and the second demodulator at the head-end node.

34. The method recited in claim 32, wherein the motion detector is incorporated in the video processor and the video processor analyzes a first portion of an image frame for changes and disregards a second portion of the image frame, the method further comprises:
comparing a portion of the second captured image frame to a corresponding portion of the first captured image frame for changes between the images frames in the portion of the captured image frames indicating the presence of motion in the surveillance area; and
issuing a motion indication.

35. The method recited in claim 32, the method further comprises:
receiving a transmission error for the video sensory electrical signals; and
saving the first captured image frame to the memory.

36. The method recited in claim 32, wherein the motion detector is incorporated in the video processor and the video processor compares image frames for changes indicating the presence of motion between capture of the image frames, the method further comprises:
comparing the second captured image frame to the first captured image frame for changes indicating the presence of motion in the surveillance area; and
issuing a motion indication.

37. The method recited in claim 36, wherein issuing a motion indication from comparing the second captured image frame to the first captured image frame for change between the second captured image frame and the first captured image frame further comprises:
measuring an amount of change between the second captured image frame and the first captured image frame; and
comparing the measured amount of change to a predetermined threshold amount of change.

38. A system for implementing video surveillance on an existing coaxial network, comprising:
a coaxial network;
a plurality of a surveillance control devices coupled to the coaxial network, each control device comprising:
a data port for connecting to the coaxial network;
a modulator for modulating first digital signals onto the first carrier signal, wherein at least some of said first digital signals representing sensory electrical signals, said modulator electrically coupled to the data port;
a demodulator for demodulating second digital signals off the second carrier signal, said demodulator electrically coupled to the data port;
a memory for storing sensory electrical signals as data;
a video sensor for capturing image frames of a surveillance area and for converting said image frames to video sensory electrical signals;
a motion detector for detecting motion in at least a portion of the surveillance area and issuing a motion indication; and
a video processor for receiving the video sensory electrical signals representative of the image frames from the video sensor and determining which image frames to save as data in the memory based on the motion indication from the motion detector;
a monitor control device coupled to the coaxial network, comprising:
a second data port for connecting to the coaxial network;
one of an RF output port and a video output port;
a second modulator electrically coupled to the second data port for modulating first digital signals onto the first carrier signal;
a second demodulator electrically coupled to the second data port for demodulating second digital signals off the second carrier signal;
a second memory; and
a video monitor coupled to the one of an RF output port and a video output port; and
a head-end, comprising:
a cable modem termination system for receiving first digital signals on the first carrier signal and transmitting second digital signals on the second carrier signal; and
a temporary storage for storing image frames of a surveillance area.

39. The system recited in claim 38, wherein the video processor in each of the plurality of surveillance control devices is one of a physical component residing in the device, a physical component residing in the video sensor and video processing executable instructions residing in the memory for processing by the logic circuitry.

40. The system recited in claim 38, wherein each of the plurality of surveillance control devices further comprises an RFID reader for reading RF tags.

41. The system recited in claim 38, wherein the video sensor in each of the plurality of surveillance control devices is a quasi night vision sensor for operating in low light.

42. The system recited in claim 38, wherein each of the plurality of surveillance control devices further comprises a medical monitoring device port.

43. The system recited in claim 38, wherein each of the plurality of surveillance control devices further comprises a wireless access point for sending and receiving wireless signals.

44. The system recited in claim 43, wherein the wireless access point is compliant with one of IEEE 802.11, Wireless Personal Area Network (WPAN), Bluetooth, HOME Radio Frequency (HomeRF) and HIPERLAN standards.

45. The system recited in claim 38, wherein each of the plurality of surveillance control devices further comprises a remote user interface for receiving user commands.

46. The system recited in claim 45, wherein the remote user interface further comprises a "PRIVACY" key for disabling the video sensor.

47. The system recited in claim 38, wherein the motion detector in each of the plurality of surveillance control devices is incorporated in the respective video processor and the video processor compares image frames for changes indicating the presence of motion in the surveillance area between capture of the image frames.

48. The system recited in claim 47, wherein the video processor analyzes a first portion of an image frame for changes and disregards a second portion of the image frame.

49. The system recited in claim 47, wherein the video processor selects at least some image frames for discarding based on the comparison of image frames for changes.

50. The system recited in claim 47, wherein the video processor selects at least some image frames for storage in the memory based on an amount of change detected between a current frame and a previous frame being above a predetermined threshold amount of change.

* * * * *